(12) United States Patent
Shemesh et al.

(10) Patent No.: US 10,736,570 B2
(45) Date of Patent: Aug. 11, 2020

(54) METHODS CIRCUITS ASSEMBLIES DEVICES SYSTEMS FACETS AND ASSOCIATED MACHINE EXECUTABLE CODE FOR DETECTING VITAL SIGNS

(71) Applicant: CardiacSense Ltd., Caesarea (IL)

(72) Inventors: Eldad Shemesh, Binyamina (IL); Igor Kouperman, Yokneam (IL); Boris Spektor, Haifa (IL)

(73) Assignee: CARDIACSENSE LTD., Caesarea (IL)

( * ) Notice: Subject to any disclaimer, the term of this patent is extended or adjusted under 35 U.S.C. 154(b) by 263 days.

(21) Appl. No.: 15/666,759

(22) Filed: Aug. 2, 2017

(65) Prior Publication Data
US 2018/0035943 A1 Feb. 8, 2018

Related U.S. Application Data

(63) Continuation-in-part of application No. 15/079,084, filed on Mar. 24, 2016, now abandoned.
(Continued)

(51) Int. Cl.
*A61B 5/00* (2006.01)
*A61B 5/0402* (2006.01)
(Continued)

(52) U.S. Cl.
CPC ............ *A61B 5/681* (2013.01); *A61B 5/0205* (2013.01); *A61B 5/0245* (2013.01); *A61B 5/02055* (2013.01); *A61B 5/02416* (2013.01); *A61B 5/02438* (2013.01); *A61B 5/0402* (2013.01); *A61B 5/117* (2013.01); *A61B 5/14551* (2013.01); *A61B 5/721* (2013.01); *A61B 5/7203* (2013.01); *A61B 5/742* (2013.01); *A61B 5/02125* (2013.01); *A61B 5/02405* (2013.01);
(Continued)

(58) Field of Classification Search
CPC ........ B60K 31/00; B60K 31/18; G01C 21/00; A61B 5/14551; A61B 5/14532; A61B 2576/00; A61B 5/026; A61B 5/1455; A61B 5/7221; A61B 5/725; A63B 2024/0012; A63B 2220/805
See application file for complete search history.

(56) References Cited

U.S. PATENT DOCUMENTS 9,874,862 B2 * 1/2018 Lee .................. G05B 15/02
2007/0276270 A1 11/2007 Tran
(Continued)

FOREIGN PATENT DOCUMENTS

WO 2018025199 A1 2/2018
WO 2019215723 A1 11/2019

*Primary Examiner* — Michael W Kahelin
*Assistant Examiner* — Shirley X Jian
(74) *Attorney, Agent, or Firm* — Dorsey & Whitney LLP

(57) ABSTRACT

Disclosed are a composite bio-parameter sensor assembly and a wearable device including same, for detecting vital signs of a subject person. The sensor assembly includes one or more sensors, mounted on an outer contact surface of the assembly, having a sensing surface to optically detect one or more parameters of a pulse of the subject. The sensor assembly further includes an additional sensor, facing an inner cavity of the assembly, for optically detecting displacement of the one or more outer sensors. The one or more sensors and the additional sensor are positioned on the opposite sides of a printed circuit board (PCB).

21 Claims, 18 Drawing Sheets

Related U.S. Application Data

(60) Provisional application No. 62/369,765, filed on Aug. 2, 2016, provisional application No. 62/393,688, filed on Sep. 13, 2016.

(51) Int. Cl.
    *A61B 5/1455*     (2006.01)
    *A61B 5/024*     (2006.01)
    *A61B 5/0205*     (2006.01)
    *A61B 5/117*     (2016.01)
    *A61B 5/0245*     (2006.01)
    *A61B 5/0464*     (2006.01)
    *A61B 5/145*     (2006.01)
    *A61B 5/08*     (2006.01)
    *A61B 5/021*     (2006.01)

(52) U.S. Cl.
CPC ........... *A61B 5/0464* (2013.01); *A61B 5/0816* (2013.01); *A61B 5/14532* (2013.01); *A61B 5/14542* (2013.01); *A61B 5/4818* (2013.01); *A61B 5/6803* (2013.01); *A61B 5/6826* (2013.01); *A61B 5/6844* (2013.01); *A61B 5/6893* (2013.01); *A61B 5/6895* (2013.01); *A61B 2562/0219* (2013.01); *A61B 2562/0233* (2013.01)

(56) References Cited

U.S. PATENT DOCUMENTS

| | | |
|---|---|---|
| 2008/0071180 A1 | 3/2008 | Borgos |
| 2008/0181556 A1 | 7/2008 | Borgos et al. |
| 2011/0232388 A1 | 9/2011 | Butterfield |
| 2013/0310700 A1 | 11/2013 | Wiard et al. |
| 2014/0257049 A1 | 9/2014 | Soundarapandian et al. |
| 2014/0275850 A1 | 9/2014 | Venkatraman et al. |
| 2014/0275852 A1 | 9/2014 | Hong et al. |
| 2015/0230735 A1 | 8/2015 | Venkatraman et al. |
| 2015/0261946 A1 | 9/2015 | Yoon et al. |
| 2016/0029911 A1 | 2/2016 | Lee |
| 2016/0070245 A1* | 3/2016 | Lee .................... G05B 15/02 700/49 |
| 2016/0183818 A1 | 6/2016 | Richards et al. |
| 2016/0317067 A1 | 11/2016 | Lee |
| 2017/0020399 A1 | 1/2017 | Shemesh et al. |
| 2017/0135633 A1 | 5/2017 | Connor |
| 2018/0146870 A1 | 5/2018 | Shemesh et al. |

* cited by examiner

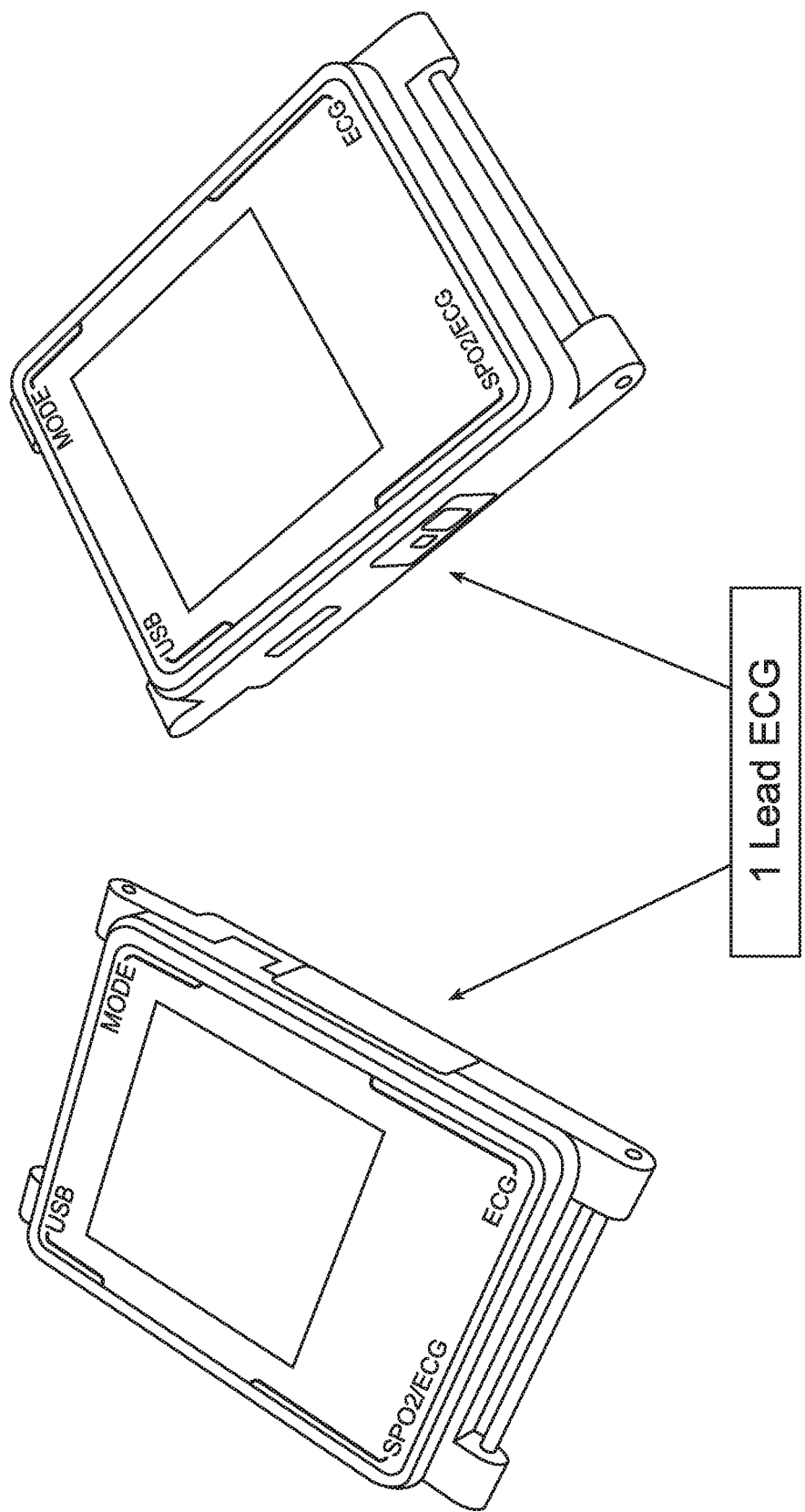

METHODS CIRCUITS ASSEMBLIES DEVICES SYSTEMS FACETS AND ASSOCIATED MACHINE EXECUTABLE CODE FOR DETECTING VITAL SIGNS

RELATED APPLICATIONS

The present invention claims priority from the following U.S. Provisional Patent Applications: Application No. 62/369,765 filed Aug. 2, 2016; and Application No. 62/393,688 filed Sep. 16, 2016. Additionally, the present invention claims the benefit of U.S. Utility patent application Ser. No. 15/079,084 filed Mar. 24, 2016. All of the above listed applications are hereby incorporated by reference in their entirety.

FIELD OF THE INVENTION

The present invention generally relates to the fields of biological sensing, medical diagnostics, and bio-parameter based authentication. More specifically, the present invention relates to methods, circuits, assemblies, devices, systems, facets and associated machine executable code for detecting vital signs.

BACKGROUND

Measurement of various biometric parameters has uses ranging from basic healthcare related diagnostics to person/subject authentication for commerce and security. To date, noninvasive measurement of a person's hemodynamic parameters, such as blood pressure, has presented significant technical challenges.

Beyond the obvious need for healthcare diagnostics, authentication is an important element in today's massive use of electronic commerce. It is also becoming more and more important for security related applications. One of the biggest problems in electronic commerce is identity theft and/or credit card information theft. In order to mitigate the risk of such theft, collection of additional, unforgeable authentication elements are needed. As of today, the only biometric parameters readily collected for purposes of identification or authentication is fingerprints, which fingerprints are prone to relatively easy cloning or spoofing.

In general, artifacts, or biological parameter measurement related artifacts, pertain to biological values observed in a scientific or medical investigation that are not naturally present, or to recorded activity that is not of the examined origin, but rather occur as a result of the investigative procedure or means and/or the effect of other factors on them.

Artifacts on an electrocardiogram (ECG) can result from a variety of internal and external causes. In some cases troubleshooting the problem may be straightforward, in many cases, however, artifacts mimic ECG abnormalities and may cause inaccuracies in the values of the measured parameters and may result in erroneous diagnostics.

Some of the more common types of artifacts in ECG tracings include: Loose lead artifact may result from the ECG electrodes not sticking/in-contact to/with the subject's body or skin; Wandering baseline artifact presents as a slow, undulating baseline on the electrocardiogram, it may be caused by movements of the examined subject, including breathing; Muscle tremor (or tension) artifact is a type of motion artifact that may be caused by a subject's voluntary movements or body positions involving muscle contraction, or by external factors resulting in muscle contraction, such as a cold environment causing the shivering of the subject; and Electromagnetic interference (EMI) artifact usually results from electrical power lines, electrical equipment and/or external electro-magnetic effect, for example from mobile telephones. Additional artifact types may include: CPR compression artifact, Neuromodulation artifact, Echo distortion artifact and Arterial pulse tapping artifact.

The calculation of arterial oxygen saturation (SpO2) relies on the amplitude information of the high-quality photoplethysmographic (PPG) signals, which could be contaminated by motion artifacts (MA) during monitoring.

Pulse oximeter has been widely utilized to measure the level of arterial oxygen saturation (SpO2) and pulse rate (PR) of humans noninvasively. It is based on the principles: 1) the different light absorption properties between oxyhemoglobin (HbO2) and deoxyhemoglobin (Hb): 2) only the arterial blood (provided that the mildly pulsatile venous blood can be neglected) pulsate in the tissue contributing to the pulsation of emergent light intensity (termed AC part), while others correspond to the emergent light intensity baseline (termed DC part).

The measurement positions of pulse oximeter are usually fingertips, earlobes, toes, foreheads, etc., since the capillary network of these parts are abundant. A pulse oximeter is precise provided with clean PPG signals, which are related to the blood volume changes in the microvascular bed of tissue. It is not a trivial task, however, to acquire interference-free clean PPG signals in real-world applications. Numerous factors, such as MA, ambient lights, low perfusion and temperature variations could lead to pulse oximeters' performance degradation. In particular, the removal of MA, which is caused by voluntary or involuntary movements of the subject during the measurement, is always challenging ever since the appearance of pulse oximeters.

Conventional filters are often incapable of getting rid of MA effectively, for example, due to the frequency overlaps between the MA and clean PPG signal. Researchers have developed numerous approaches to tackle this issue. The Motion Average Filtering (MAF) method is mainly directed at suppressing the sporadically occurring noise in the corrupted PPG signals. Adaptive filters, which may adjust their weight vector based on adaptive algorithms, are tools to deal with the in-band noise, provided that the reference signal (which is either correlated with the MA part but uncorrelated with PPG signal or correlated with the clean PPG signal but uncorrelated with the MA) is available. One way to obtain the reference signal is with the help of extra hardware such as accelerometers or photoelectric devices.

Another way is to synthesize the reference signal from the two channel contaminated PPG signals. In consideration of the non-stationarity of PPG signals, wavelet transform is performed to remove MA. The empirical mode decomposition (EMD), which is another decomposition to handle non-stationary signal, is another. Although these two methods could reduce the MA to some extent, both of them are troubled with the problem of how to select an appropriate threshold to decide which components should be removed. High order statistics are used to extract clean artifact-free PPG signals preserving all the essential morphological features required.

Applying cycle-by-cycle Fourier series analysis (CFSA) to deal with MA may also demonstrate a satisfying performance. The period of every PPG signal cycle, however, must be acquired precisely when applying CFSA methods. Based on the independence between the PPG signal and the MA, Independent Component Analysis (ICA) combining a signal enhancement preprocessor is used to separate the PPG signal from the contaminated original PPG signal, from which the efficacy of the ICA algorithm in dealing with the MA corrupted PPG signals could be confirmed. Despite the usually good performance of the ICA method, one must keep in mind that the ICA has permutation and scale ambiguities. Meanwhile, the SpO2 computation needs the accurate amplitude information of both the red and IR light channel PPG signals, the ICA output cannot be used to calculate the SpO2 value directly.

There remains a need, in the fields of biological sensing, medical diagnostics and bio-parameter based authentication, for solutions facilitating the accurate collection of biometric parameters, for the estimation of biological parameters, such as the estimation of hemodynamic parameters of a subject, for medical purposes and/or authentication or identification purposes.

SUMMARY OF THE INVENTION

The present invention includes methods, circuits, assemblies, devices, systems, facets and associated machine executable code for detecting vital signs and for artifact cancellation/mitigation. A wearable device, for example in the form of a watch/wristband, may include a composite sensor assembly for measuring or detecting bio-parameters and vital signs of a subject. The composite sensor assembly, and/or the wearable device including same, may include one or more sensors for artifact cancellation/mitigation.

According to embodiments of the present invention, there may be provided a set of two or more bio-parameter sensors, each sensor of a different sensor type and adapted to sense a different biological parameter of a user. Sensors of different sensor types may be operated in a synchronous manner in order to obtain measurements usable for deriving a biological parameter which is not measurable by any of the operated sensors individually. According to embodiments, each of two or more bio-parameter sensors, of different sensor types, may be operated by control circuitry which is integral or otherwise functionally associated with control circuitry of the other. According to embodiments, two or more of the bio-parameter sensors, of different sensor types, may be part of a common sensor assembly, which sensor assembly may be referred to as a composite sensor assembly. The composite sensor assembly according to embodiments of the present invention may hold two or more of the sensors of different sensor types in a position and orientation relative to each other and relative to a contact surface of the assembly such that both sensors are brought into contact with a contact surface (e.g. skin) of a subject (e.g. person) whose biological parameter is being sensed or derived. The one or more sensors for artifact cancellation/mitigation may likewise be in a position and orientation relative to each other and relative to a contact surface of the assembly such that both sensors are brought into contact with a contact surface (e.g. skin) of a subject (e.g. person) whose biological parameter is being sensed or derived; and/or, may be positioned at a different internal location of the assembly or the wearable device.

A composite sensor assembly according to some embodiments may include any combination of optical sensors, electrical resistivity sensors, electrocardiogram (ECG) sensors, mechanical pressure sensors, motion sensors (e.g. accelerometers, gyroscopes and magnetometers), temperature sensors, Galvanic Skin Response (GSR) sensors and any other sensor usable for measuring a biological parameter and/or for artifact cancellation/mitigation. According to embodiments, a first sensor integral or otherwise functionally associated with the composite assembly may be an electrocardiogram (ECG) type sensor which may detect electrical signals generated in connection with and/or during a user's heart beats. According to the same embodiment, a second sensor integral or otherwise functionally associated with the composite assembly may be a photoplethysmogram (PPG) type sensor which may optically sense a user's pulse as blood passes through an arterial of the user which is being optically inspected and/or optically monitored by the PPG. Each respective sensor may include at least one respective sensor element and at least one respective sensing circuit, which sensing circuits may be integral or otherwise functionally associated with one another.

An exemplary sensor assembly, in accordance with some embodiments, may include one or more PPG sensor(s) mounted on an outer contact surface/facet of the assembly and an optical motion/displacement/pressure sensor facing an inner cavity of the assembly and the wearable device. Both, outer and inner sensors, may be positioned on the opposite sides of the same printed circuit board (PCB), which printed circuit board may be suspended on springs or a flexible surface connecting the PCB to a chassis of the assembly. The chassis of the assembly may be part of, and connected to, a wearable device (e.g. a wristband/watch) intended to hold/retain the assembly against a body part, for example the wrist of a subject (device wearing user).

According to some embodiments, the wearable device may include one or more ECG sensors, as part of the composite sensor assembly or as a separate unit(s) functionally associated therewith. According to some embodiments. ECG sensor electrodes, of at least some of the ECG sensors, may be positioned next to the PPG assembly, on the downward (subject skin) facing contact surface/side/facet of the suspended PCB of the assembly, optionally on the same plane, such that both, the PPG's emitters and photodiodes and the ECG's electrodes, come in contact with the skin of the user—as a result of their positioning and/or by the downward press/push of the flexible surface against the skin of the wearing subject.

According to some embodiments, the wearable device may further include one or more additional/external ECG electrodes, raised (i.e. further away from the subject's skin) in relation to the plane of the PPG's emitters and photodiodes and the ECG's down (skin) facing electrodes. Raised ECG electrodes may, for example, include two electrodes, or electrode batches/sets, on the sides of the wearable device—for example on its right and left sides—and a third electrode that may be used as a reference electrode for background noise cancellation/compensation. The reference electrode may be used for picking up reference noise and measuring it using respective ECG sensor processing circuitry connected to the reference electrode, wherein measured values may be used for cancellation/compensation of noise in the measured electric cardio activity of the examined subject, as picked up by the down facing and external electrodes and measured by the sensor data processing circuitry of the ECG sensor(s).

A system, in accordance with some embodiments, may further include one or more external PPG and/or ECG signals pickup kits or units, connectable to the wearable device by an electric wire(s). The PPG/ECG units may allow for continuous PPG SpO2 and/or continuous ECG measurements, by providing additional and constant signal pickup locations on the subject's body.

The wearable device, in accordance to some embodiments, or the composite sensor assembly thereof, may consist of a composite electrical and optical configuration of sensors, including one or more ECG sensors for deriving cardio electric activity measurements and one or more PPG sensors for deriving SpO2 measurements. The composite electrical and optical configuration of sensors may further include one or more thermal sensors for calibrating, normalizing and/or compensating for variations in SpO2 measurement levels, derived by the PPG sensor(s), based on measured skin temperature and/or core body temperature of the examined, device wearing, subject.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 2F-2G, are diagrams of an exemplary wearable wristband device (shown without band/strap) having two electrodes positioned on its right side (FIG. 2F) and on its left side (FIG. 2G), in accordance with some embodiments of the present invention;

Figure 1:
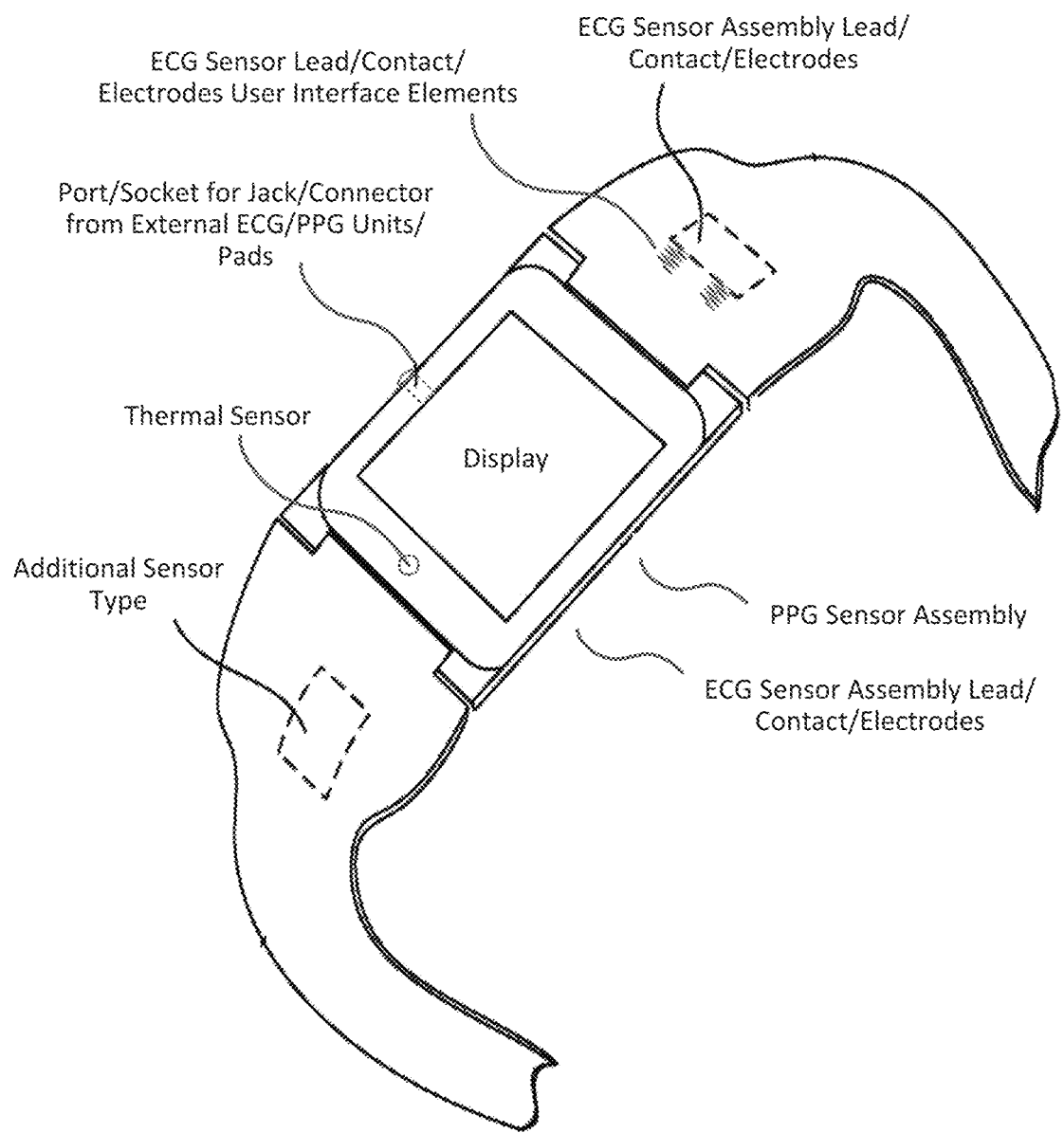
FIG. 1, is a schematic diagram of an exemplary wearable device with a composite bio-sensor assembly, in accordance with some embodiments of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of some embodiments. However, it will be understood by persons of ordinary skill in the art that some embodiments may be practiced without these specific details. In other instances, well-known methods, procedures, components, units and/or circuits have not been described in detail so as not to obscure the discussion.

Unless specifically stated otherwise, as apparent from the following discussions, it is appreciated that throughout the specification discussions utilizing terms such as "processing", "computing", "calculating", "determining", or the like, may refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

In addition, throughout the specification discussions utilizing terms such as "storing", "hosting", "caching", "saving", or the like, may refer to the action and/or processes of 'writing' and 'keeping' digital information on a computer or computing system, or similar electronic computing device, and may be interchangeably used. The term "plurality" may be used throughout the specification to describe two or more components, devices, elements, parameters and the like.

Some embodiments of the invention, for example, may take the form of an entirely hardware embodiment, an entirely software embodiment, or an embodiment including both hardware and software elements. Some embodiments may be implemented in software, which includes but is not limited to firmware, resident software, microcode, or the like.

Furthermore, some embodiments of the invention may take the form of a computer program product accessible from a computer-usable or computer-readable medium providing program code for use by or in connection with a computer or any instruction execution system. For example, a computer-usable or computer-readable medium may be or may include any apparatus that can contain, store, communicate, propagate, or transport the program for use by or in connection with the instruction execution system, apparatus, or device.

In some embodiments, the medium may be an electronic, magnetic, optical, electromagnetic, infrared, or semiconductor system (or apparatus or device) or a propagation medium. Some demonstrative examples of a computer-readable medium may include a semiconductor or solid state memory, magnetic tape, a removable computer diskette, a random access memory (RAM), a read-only memory (ROM), a rigid magnetic disk, and an optical disk. Some demonstrative examples of optical disks include compact disk-read only memory (CD-ROM), compact disk-read/write (CD-R/W), and DVD.

In some embodiments, a data processing system suitable for storing and/or executing program code may include at least one processor coupled directly or indirectly to memory elements, for example, through a system bus. The memory elements may include, for example, local memory employed during actual execution of the program code, bulk storage, and cache memories which may provide temporary storage of at least some program code in order to reduce the number of times code must be retrieved from bulk storage during execution.

In some embodiments, input/output or I/O devices (including but not limited to keyboards, displays, pointing devices, etc.) may be coupled to the system either directly or through intervening I/O controllers. In some embodiments, network adapters may be coupled to the system to enable the data processing system to become coupled to other data processing systems or remote printers or storage devices, for example, through intervening private or public networks. In some embodiments, modems, cable modems and Ethernet cards are demonstrative examples of types of network adapters. Other suitable components may be used.

Functions, operations, components and/or features described herein with reference to one or more embodiments, may be combined with, or may be utilized in combination with, one or more other functions, operations, components and/or features described herein with reference to one or more other embodiments, or vice versa.

General

The present invention includes methods, circuits, assemblies, devices, systems, facets and associated machine executable code for detecting vital signs and for artifact cancellation/mitigation through compensation. A wearable device, for example in the form of a watch/wristband, may include a composite sensor assembly for measuring or detecting bio-parameters and vital signs of a subject. The composite sensor assembly may include one or more sensors for artifact cancellation/mitigation through compensation.

According to embodiments of the present invention, there may be provided a set of two or more bio-parameter sensors, each sensor of a different sensor type and adapted to sense a different biological parameter of a user. Sensors of different sensor types may be operated in a synchronous manner in order to obtain measurements usable for deriving a biological parameter which is not measurable by any of the operated sensors individually. According to embodiments, each of two or more bio-parameter sensors, of different sensor types, may be operated by control circuitry which is integral or otherwise functionally associated with control circuitry of the other. According to embodiments, two or more of the bio-parameter sensors, of different sensor types, may be part of a common sensor assembly, which sensor assembly may be referred to as a composite sensor assembly. The composite sensor assembly according to embodiments of the present invention may hold two or more of the sensors of different sensor types in a position and orientation relative to each other and relative to a contact surface of the assembly such that both sensors are brought into contact with a contact surface (e.g. skin) of a subject (e.g. person) whose biological parameter is being sensed or derived.

A composite sensor assembly according to some embodiments may include any combination of optical sensors, electrical resistivity sensors, electrocardiogram (ECG) sensors, mechanical pressure sensors, motion sensors (e.g. accelerometers, gyroscopes and magnetometers), temperature sensors, Galvanic Skin Response (GSR) sensors and any other sensor usable for measuring a biological parameter and/or for artifact cancellation/mitigation. According to embodiments, a first sensor integral or otherwise functionally associated with the composite assembly may be an electrocardiogram (ECG) type sensor which may detect electrical signals generated in connection with and/or during a user's heart beats. According to the same embodiment, a second sensor integral or otherwise functionally associated with the composite assembly may be a photoplethysmogram (PPG) type sensor which may optically sense a user's pulse as blood passes through an arterial of the user which is being optically inspected and/or optically monitored by the PPG. Each respective sensor may include at least one respective sensor element and at least one respective sensing circuit, which sensing circuits may be integral or otherwise functionally associated with one another.

Suspended Motion and Displacement Sensor

An exemplary sensor assembly, in accordance with some embodiments, may include one or more PPG sensor(s) mounted on an outer contact surface/facet of the assembly and an optical motion/displacement/pressure sensor facing an inner cavity of the assembly and the wearable device. Both, outer and inner sensors, may be positioned on the opposite sides of the same printed circuit board (PCB), which printed circuit board may be suspended on springs or a flexible surface connecting the PCB to a chassis of the assembly. The chassis of the assembly may be part of, and connected to, a wearable device (e.g. a wristband/watch) intended to hold/retain the assembly against a body part, for example the wrist of a subject (device wearing user).

The PPG sensor(s) on the down (i.e. subject's skin) facing side of the PCB and the displacement sensor(s) on the up (i.e. assembly cavity) facing side of the PCB may accordingly be collectively correlated to the flexible surface, connecting the PCB to the chassis of the assembly. The flexible surface, and sensors correlated thereto, may be positioned substantially at the bottom (wearing subject's skin facing side/facet) of the wearable device. According to some embodiments, the flexible surface may, for example, consist of a biaxially-oriented polyethylene terephthalate (boPET) type, or a substantially similar material type, forming an elastic sheet—onto which the sensors are collectively correlated.

The flexible surface, may be stretched/bent, upon the wearable/wristband/watch being worn by a subject. The flexible/elastic properties of the surface may bias it towards its original, pre worn shape, causing it and the sensor assembly's contact surface suspended thereon, to press/push against the skin of the wearing subject. As a result, the down facing PPG sensors of the assembly may be pushed against the subject's skin, retaining substantially constant contact with the skin, or proximity to it.

According to some embodiments, the springs/flexible-surface may also absorb physical displacement forces, such as those caused by the subject's physical movements and/or the subject's pulse, such that the PPG sensor remains in substantially firm and stable contact with the subject's skin. The level of artifacts that originate from the pressure change the PPG sensor is facing during movements of the fingers/palm of the subject may be accordingly lowered.

According to some embodiments, the springs/flexible-surface may allow for the optical displacement sensor to move in sync with the PPG sensor(s). The displacement sensor may include an emitter whose emitted light is directed, up and away from the wearing subject's skin and towards a reflector placed on an inner surface of the assembly cavity substantially opposite of the emitter. The displacement sensor may also include a photodiode positioned in proximity with the emitter and configured to sense reflections of the emitter's light reflected by the reflector on the opposite side of the cavity. As the distance between the displacement sensor emitter, mounted on an inner (i.e. upper—facing away from the subject's skin) surface of the suspended PCB, and the displacement sensor reflector changes due to movements of the PCB relative to the chassis forming the cavity to which the reflector is attached, the amplitude, return time and/or phase of the light detected by the displacement sensor photodiode also changes. Accordingly, displacement/movement/pressure experienced by the PPG sensor(s) may be measured. Based on the measured displacement/movement/pressure values, artifacts/noise in the bio-parameters of the examined subject, measured by the PPG sensor(s), may be cancelled/mitigated.

According to some embodiments, the emitter, of at least some of the PPG sensors, may include a combination of three separate emitters—a red light emitter, a green light emitter and a blue light emitter; or, a combination of four separate emitters—an infra-red light emitter, a red light emitter, a green light emitter and a blue light emitter. An optical filter, in the form of a plate or a surface over/covering the photodiodes of the PPG sensors, may be tuned to have different optical band passes. The tunable optical filter may be tuned to correspond (i.e. allow the passage of) to one or more of the photon wavelengths of one or more of the red, green and/or blue emitters; or, may be tuned to correspond (i.e. allow the passage of) to one or more of the photon wavelengths of one or more of the infra-red, red, green and/or blue emitters. According to some embodiments, the above set of emitters may operate with two or more sets of photodiodes such that each emitter is positioned at a corresponding matching/suitable, or optimal, distance from its respective photodiode or photodiode area/section.

Down Facing, External and Reference ECG Electrodes

According to some embodiments, the wearable device may include one or more ECG sensors, as part of the composite sensor assembly or as a separate unit(s) functionally associated therewith. According to some embodiments, ECG sensor electrodes, of at least some of the ECG sensors, may be positioned next to the PPG assembly, on the downward (subject skin) facing contact surface/side/facet of the suspended PCB of the assembly, optionally on the same plane, such that both, the PPG's emitters and photodiodes and the ECG's electrodes, come in contact with the skin of the user—as a result of their positioning and/or by the downward press/push of the flexible surface against the skin of the wearing subject.

According to some embodiments, the wearable device may further include one or more additional/external ECG electrodes, raised (i.e. further away from the subject's skin) in relation to the plane of the PPG's emitters and photodiodes and the ECG's down (skin) facing electrodes. Raised ECG electrodes may, for example, include two electrodes, or electrode batches/sets, on the sides of the wearable device—for example on its right and left sides—and a third electrode that may be used as a reference electrode for background noise cancellation/compensation. The reference electrode may be used for picking up reference noise and measuring it using respective ECG sensor processing circuitry connected to the reference electrode, wherein measured values may be used for cancellation/compensation of noise in the measured electric cardio activity of the examined subject, as picked up by the down facing and external electrodes and measured by the sensor data processing circuitry of the ECG sensor(s).

The one or more additional/external electrodes and the reference electrode may be located at accessible positions on the wearable device, allowing their engagement/interfacing by the subject wearing the device. The additional/reference electrodes may for example be located at external positions on the device, accessible by the hand/thumb of the subject, opposite to the hand/arm on which the wearable device (e.g. wristband, watch) is being worn. As the downward facing electrodes remain in substantial permanent contact with the skin of the subject wearing the device, upon the subject making contact with one or more of the external electrodes with his opposite arm, his cardio electric activity may be picked up by the electrodes and measured by the sensor data processing circuitry of the ECG sensors.

According to some embodiments, two electrodes may face down (towards the skin/body of the subject), wherein, one of the two is the reference electrode. According to some embodiments, there may be provided a facing down reference electrode and an external reference electrode, such that even if the user/subject only touches one of the external ECG pads, the system may work flawlessly.

The external electrodes (e.g. on the sides of the wearable device) may be positioned over a button/interface-element/thumb-press-button, for example in the form of a spring or a metal dome, that may sense the contact of an engaging subject and in response, signal a controller of the composite sensor assembly or the wearable device to trigger ECG measurements of the subject.

Continuous PPG/ECG Measurement

A system, in accordance with some embodiments, may further include one or more external PPG and/or ECG signals pickup kits or units, connectable to the wearable device by an electric wire(s). The PPG/ECG units may allow for continuous PPG SpO2 and/or continuous ECG measurements, by providing additional and constant signal pickup locations on the subject's body.

An external ECG signals pickup unit, in accordance with some embodiments, may include: an ECG pad and electrode(s) connectable/attachable to the chest of the examined, device wearing, subject; a connector/jack for connection to a complementary port/socket on the wearable device; and electric wire(s) for connecting there between and passing/relaying signals picked up at the ECG pad to a controller/processing-circuitry of the composite sensor assembly or the wearable device.

An external PPG signals pickup unit, in accordance with some embodiments, may include: a finger clip/connector—having one or more LED(s) and one or more photodiode(s)—connectable/attachable to the finger of the examined, device wearing, subject; a connector/jack for connection to a complementary port/socket on the wearable device; and electric wire(s) for connecting there between and passing/relaying electric signals picked up at the photodiode(s) to a controller/processing-circuitry of the composite sensor assembly or the wearable device.

According to some embodiments, the external ECG signals pickup unit and/or the external PPG signals pickup unit may take the form of passive units, adapted solely for the pickup and relaying of electric signal, wherein all processing and/or analysis of the signals is performed by a sensor data processing circuitry on the wearable device or the composite sensor assembly thereof.

The ECG pad of an external PPG signals pickup unit, in accordance with some embodiments, may consist of a combined/multi-sensor ECG and PPG pad, incorporating PPG sensor pickup components, including at least one or more emitters and one or more photodiodes, into the ECG pad. The combined pad, may be attached to a body part/organ, for example the chest, of the examined, device wearing, subject—allowing the, optionally continuous, measurement of both ECG, PPG and additional derived vital-signs/bio-parameters measurements based thereof. The additional measurements, based on PPG signals from the combined pad, may enable improved and/or more accurate vital-signs/bio-parameters measurements, for example, in cases where the examined, device wearing, subject suffers-from/has low blood perfusion in his limbs and/or fingers, hindering the PPG measurements derived based on the down facing PPG sensor(s) and/or the finger clip/connector PPG sensors of the wearable device.

Thermal Sensors

The wearable device, in accordance to some embodiments, or the composite sensor assembly thereof, may consist of a composite electrical and optical configuration of sensors, including one or more ECG sensors for deriving cardio electric activity measurements and one or more PPG sensors for deriving SpO2 measurements. The composite electrical and optical configuration of sensors may further include one or more thermal sensors for calibrating, normalizing and/or compensating for variations in SpO2, and/or other PPG applications, measurement levels, derived by the PPG sensor(s), based on measured skin temperature and/or core body temperature of the examined, device wearing, subject.

The one or more thermo-sensors may be of an optical thermal sensor type. The optical thermal sensor(s) may be located at an external/outer position of/on the wearable device and may be functionally connected with the other (e.g. PPG, ECG) sensors incorporated into the device and/or with processing/control circuitries thereof. The external/outer optical thermal sensor(s) may point outside and away of the device, such that at least a light emitter(s) and a photodiode(s) of the sensor(s) are externally directed, enabling the wearing/examined subject to direct them towards a body location or organ allowing core body temperature measurement, for example, the open mouth of the subject.

The optical thermal sensor(s) may be located at an external/outer position of/on the wearable device. The external/outer optical thermal sensor(s) may point outside and away of the device, such that at least a light emitter(s) and a photodiode(s) of the sensor(s) are externally directed and adapted for finger temperature measurement, by enabling the wearing/examined subject to engage/interface it/them by making contact with the sensor, using a finger of the hand opposite to the hand/arm on which the wearable device is being worn.

FIGURE DESCRIPTIONS

Turning to FIG. 1, there is shown an illustration of an exemplary wearable device including one or more composite sensor assemblies according to embodiments of the present invention. The device shown in FIG. 1 includes an ECG sensor assembly, a PPG sensor assembly and a motion/displacement/pressure sensor integral or otherwise functionally associated with the PPG sensor assembly.

The exemplary wearable wristband device shown, further includes contacts for an ECG sensor assembly visible on the outer side of the watchband, wherein the location of a first ECG lead or contact of the ECG assembly is shown. The location of a second ECG lead or contact, placed on the inner or back surface of the watchband, is also pointed to. Also pointed to are the PPG assembly sensors which are located on the inner surface of the wristwatch band.

Upon a user/subject/wearer strapping the wristwatch band on their arm's wrist, the PPG sensors and ECG lead/electrode come in contact and touch the skin of wearer's wrist. The ECG lead/contact, which is located on an outer surface of the watchband, can be touched by a finger or palm of the wearer's other hand, such that both ECG lead/electrodes are simultaneously contacted upon a user/wearer placing his finger. An additional, outer, PPG assembly sensor is shown, for measuring SpO2 of the wearer (i.e. from his contacting finger).

Alternatively, an external ECG lead/contact/electrode can be placed in contact with the chest of the wearer and connected to the shown port/socket for jack/connector from external ECG/PPG units/pads. The shown configuration allows for the measurement of ECG and PPG signals at the same time, which in turn may allow for the estimation of the Pulse Transmit Time (PTT). The configuration shown also including the outer, wearer finger contactable, PPG sensor allowing for the measurement of SpO2.

Further shown is a thermal sensor for calibrating, normalizing and/or compensating for variations in SpO2 measurement levels, derived by the PPG sensor(s), based on measured skin temperature and/or core body temperature of the examined, device wearing, subject.

The 'additional sensor type' shown may be anyone of several different sensor types, including, but not limited to: an SpO2 sensor, a capacitance sensor, a galvanic sensor and/or others. The above sensors can be used as either main or supporting sensors that work together with a finger print sensor. According to additional embodiments the additional sensor may be a fingerprint sensor. Further shown is the display of the wristwatch for presenting sensors associated data, wearer bio-parameters derived therefrom, and/or associated notifications.

Figure 2A:
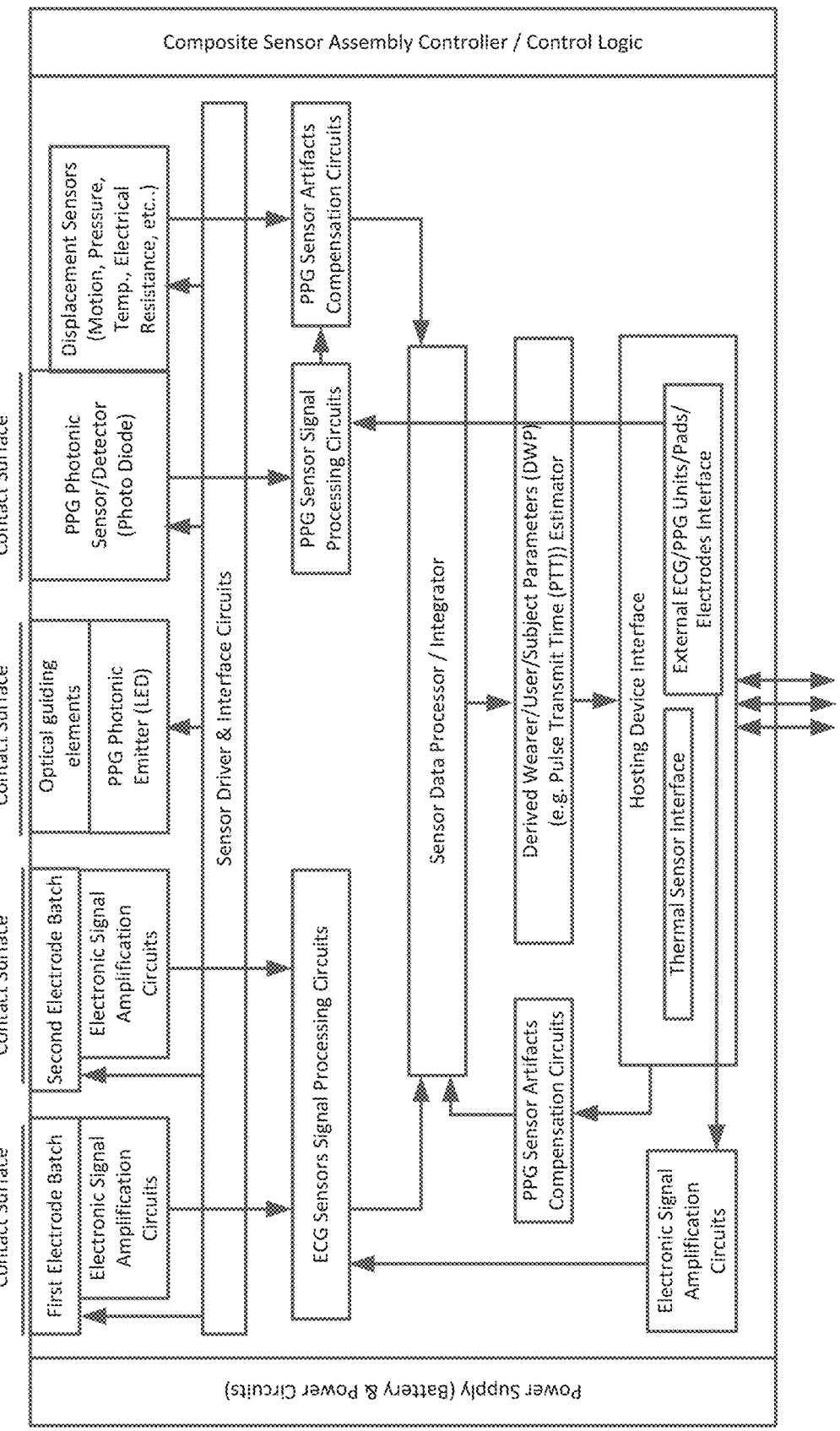
FIG. 2A, is a functional block diagram of an exemplary composite sensor assembly, in accordance with some embodiments of the present invention.

Turning now to FIG. 2A, there is shown a functional block diagram of an exemplary composite sensor assembly, in accordance with some embodiments of the present invention. The assembly shown in FIG. 2A includes an ECG sensor assembly including a first and a second electrode batch/lead/electrode and their respective signal amplification circuits. Further shown is a PPG assembly, including a photonic emitter with optical guiding elements and a photonic detector/receiver; a thermal sensor and a thermal sensor interface, connected to the shown sensor data processor; and displacement sensors.

The sensors are connected to a sensor driver and interface circuits, and the ECG and PPG sensors are connected to respective signal processing circuits. PPG sensor processed signals are relayed to compensation circuits for adjusting PPG sensor artifacts based on signals from the displacement sensors and/or from the thermal sensor interface connected to the thermal sensor (shown in FIG. 1).

Processed ECG signals and adjusted PPG signals are integrated by a mutual sensor data processor and relayed to a derived wearer/user parameter estimator for calculating bio-parameter estimations based on data from at least two of the sensors. Estimated parameters are then relayed to a hosting device interface for presentation, storage and/or further communication to a functionally associated and/or networked device/system/platform. Further shown are power supply circuits, such as a rechargeable battery, and a composite sensor assembly controller.

Figure 2B:
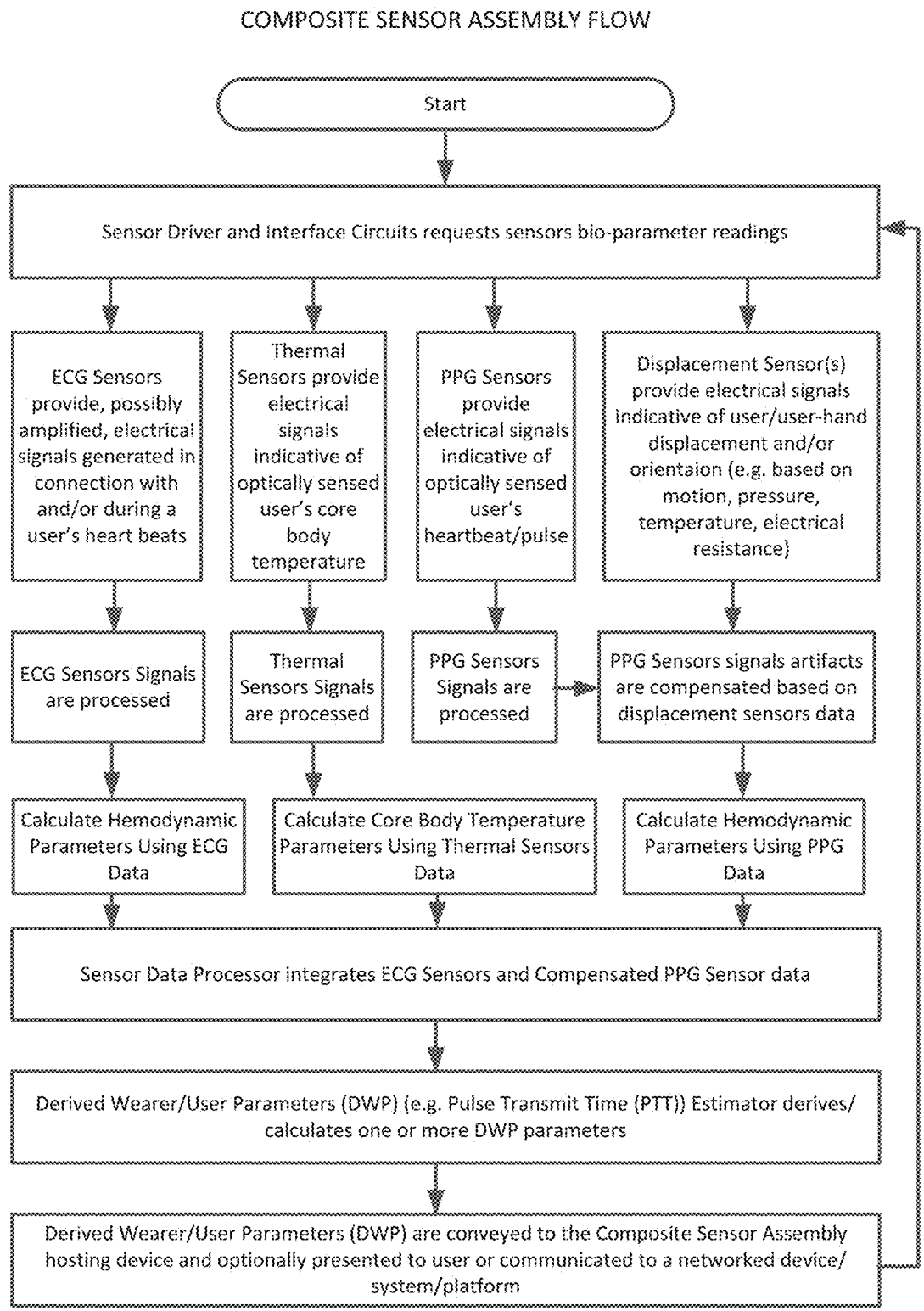
FIG. 2B, is a flowchart diagram of an exemplary composite sensor assembly operation process, in accordance with some embodiments of the present invention.

Turning now to FIG. 2B, there is shown a flowchart diagram of an exemplary composite sensor assembly operation process, in accordance with some embodiments of the present invention, including exemplary steps of operation of the sensor assembly of FIG. 2A.

Figure 2C:
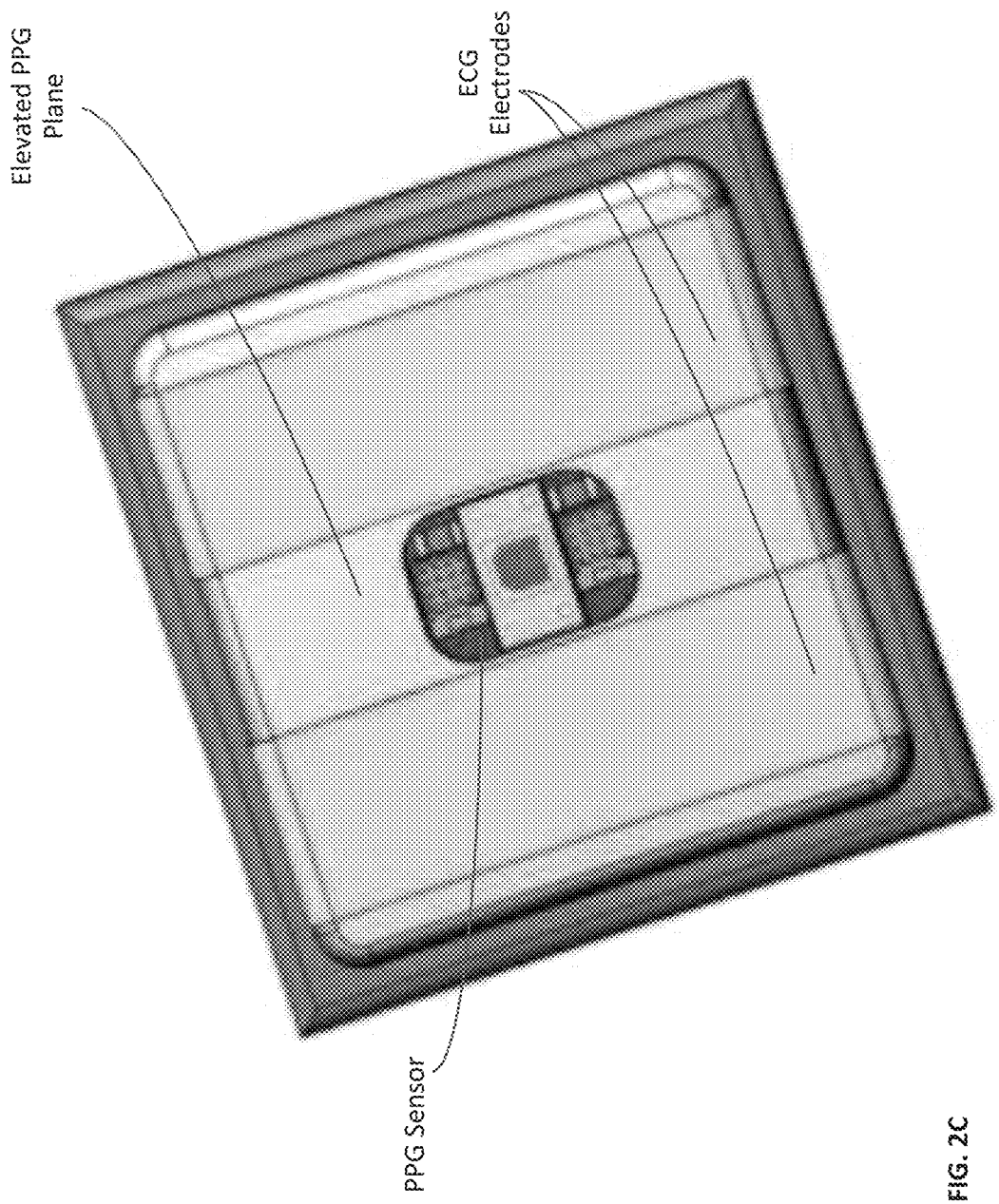
FIG. 2C, is a diagram of an exemplary composite sensor assembly—subject/user skin contact facet, in accordance with some embodiments of the present invention.

Turning now to FIG. 2C, there is shown a bottom view (viewing from the subject skin side) diagram of an exemplary composite sensor assembly—subject/user skin contact surface/facet, in accordance with some embodiments of the present invention. The ECG electrodes, of the composite sensor assembly surface/facet shown, are placed on an elevated plane of the PPG sensor such that both can come in good contact with the skin of the user/subject.

Figure 2E:
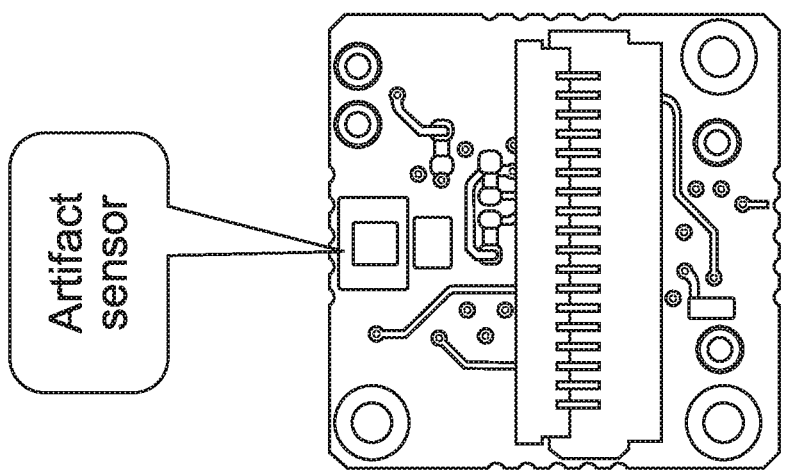
FIGS. 2D-2E, are diagrams of an exemplary implementation, wherein a PPG positioned in between two ECG pads, on one side of a PCB (FIG. 2D) and an artifact sensor on the other side of the PCB (FIG. 2E), in accordance with some embodiments of the present invention.
Figure 2D:
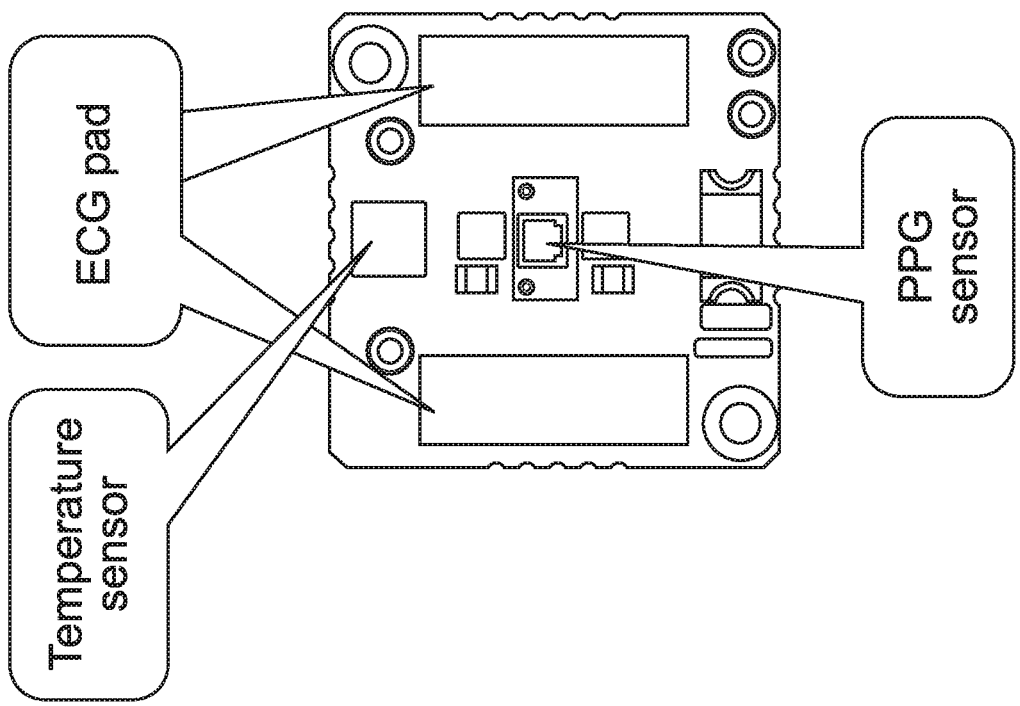

Turning now to FIGS. 2D-2E, there are shown, in accordance with some embodiments of the present invention, an exemplary implementation of a PPG positioned in between two ECG pads, on one side of a PCB (FIG. 2D); and an artifact sensor on the other side of the PCB (FIG. 2E). One of the shown ECG pads may be used as a reference, as described herein.

Turning now to FIGS. 2F-2G, there are shown, in accordance with some embodiments of the present invention, an exemplary wearable wristband device (shown without band/strap) having two electrodes positioned on its right side (FIG. 2F) and on its left side (FIG. 2G). Shown electrodes are for the fingers of the subject's hand which is opposite to the hand wearing the device. One of the shown ECG electrodes may be used as a reference, as described herein.

Figure 3A:
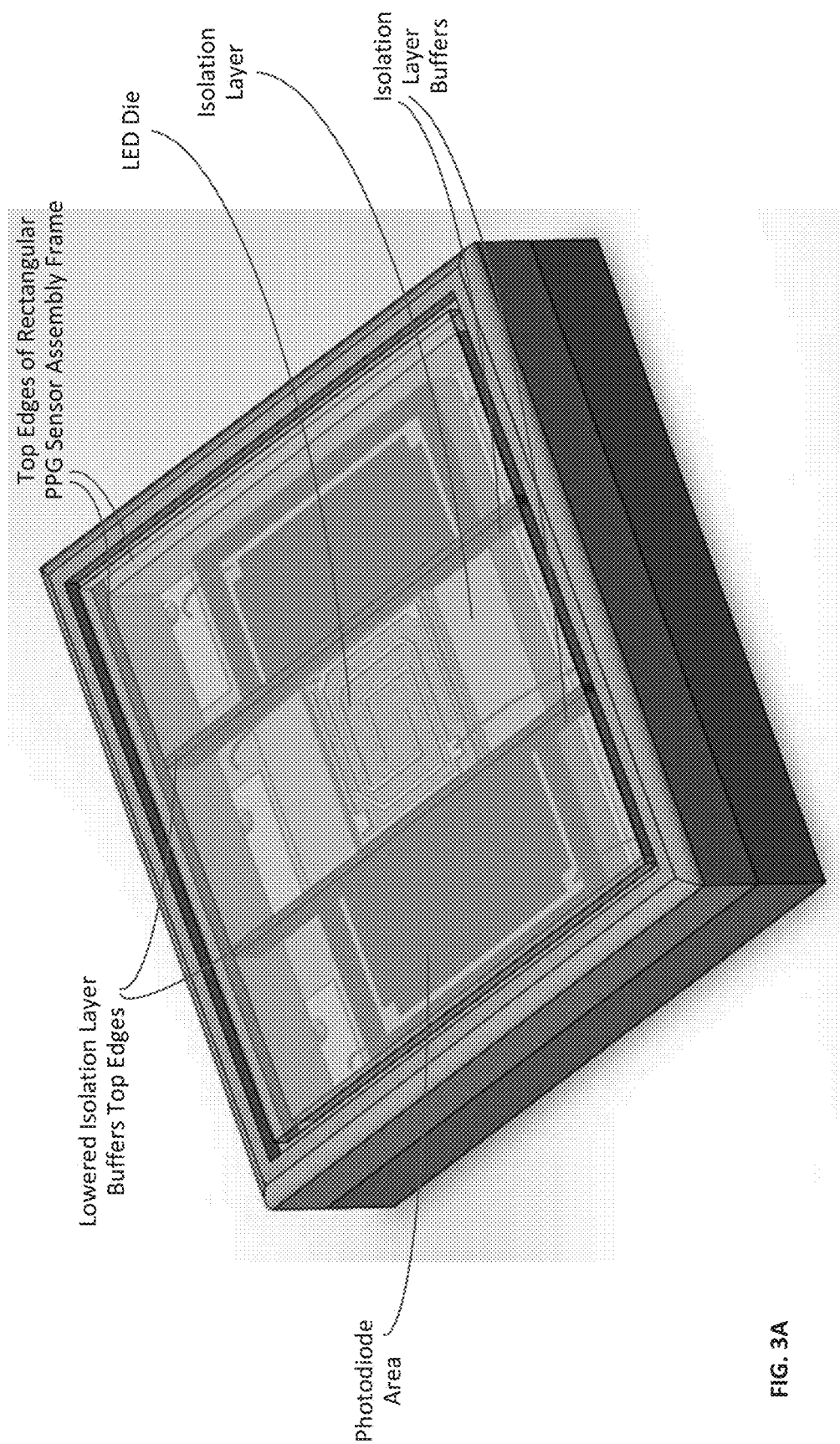
FIG. 3A, is a diagram of a first exemplary PPG sensor assembly, in accordance with some embodiments of the present invention.

Turning now to FIG. 3A, there is shown an isometric view diagram of a first exemplary PPG sensor configuration/assembly, in accordance with some embodiments of the present invention, including a PPG sensor LED die positioned substantially at the center of the assembly. The shown PPG sensor assembly further includes: an isolation layer positioned under, or below, the LED die; and two isolation layer buffers positioned on opposite sides of the LED die, for preventing light emitted from the LED die to travel back (down) and/or sideways, and to directly (i.e. not as a reflection off the examined subject's skin/tissue) hit the photodiode area (shown in black) positioned at the bottom of the assembly, under, or below, the isolation layer. The top edges of the shown isolation layer buffers are slightly lower than the top edges of the rectangular frame of the PPG sensor assembly, thus allowing for a single transparent cover to extend over substantially the entire top of the assembly.

Figure 3B:
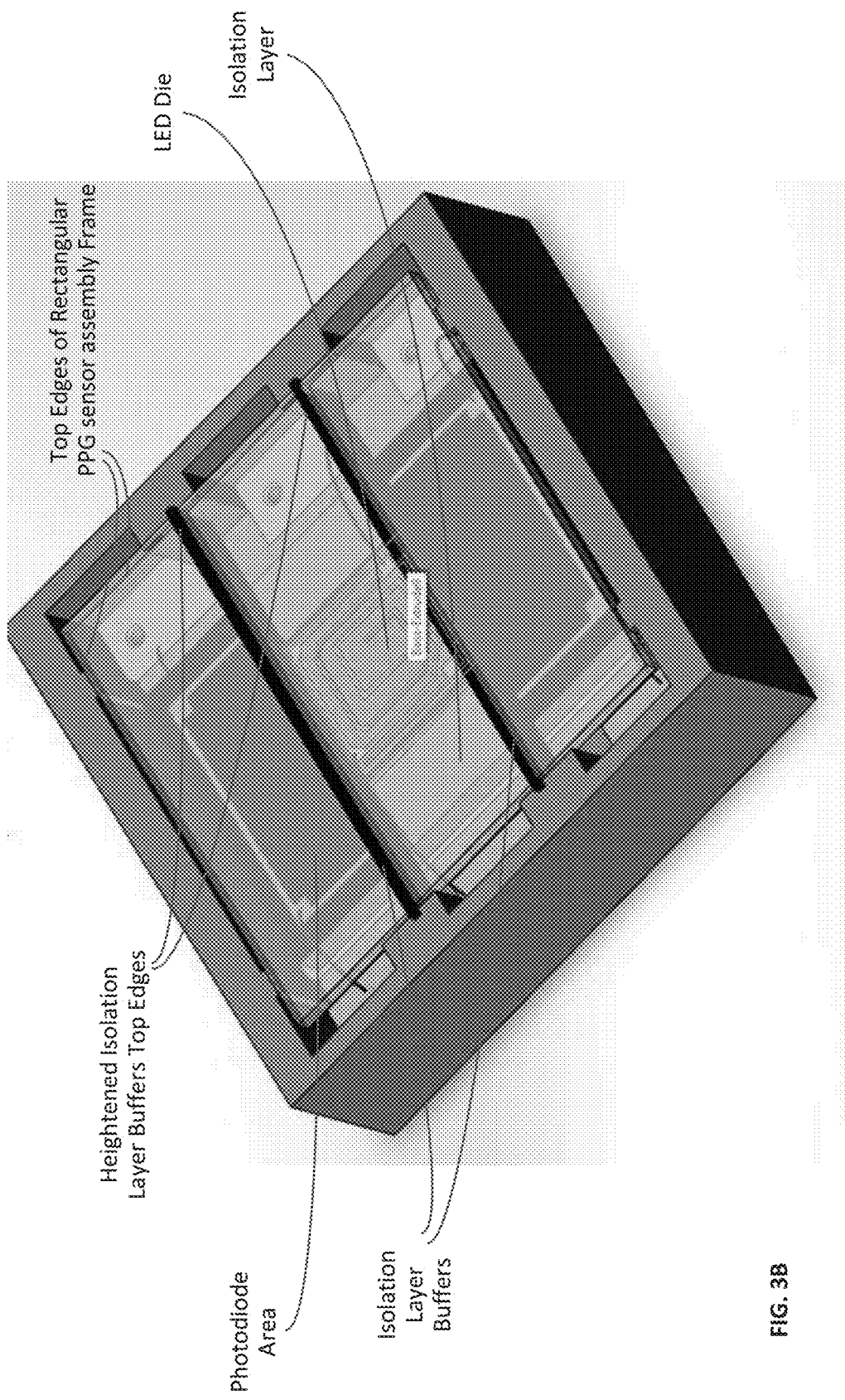
FIG. 3B, is a diagram of a second exemplary PPG sensor assembly, in accordance with some embodiments of the present invention.

Turning now to FIG. 3B, there is shown an isometric view diagram of a second exemplary PPG sensor configuration/assembly, in accordance with some embodiments of the present invention, wherein the top edges of the shown isolation layer buffers are substantially aligned with, or higher than, the top edges of the rectangular frame of the PPG sensor assembly, thus allowing for multiple (Three in this example) separate transparent covers to extend over corresponding sections, formed between the edges of the rectangular frame of the assembly and the aligned, or higher, edges of the isolation layer buffers.

Figure 3C:
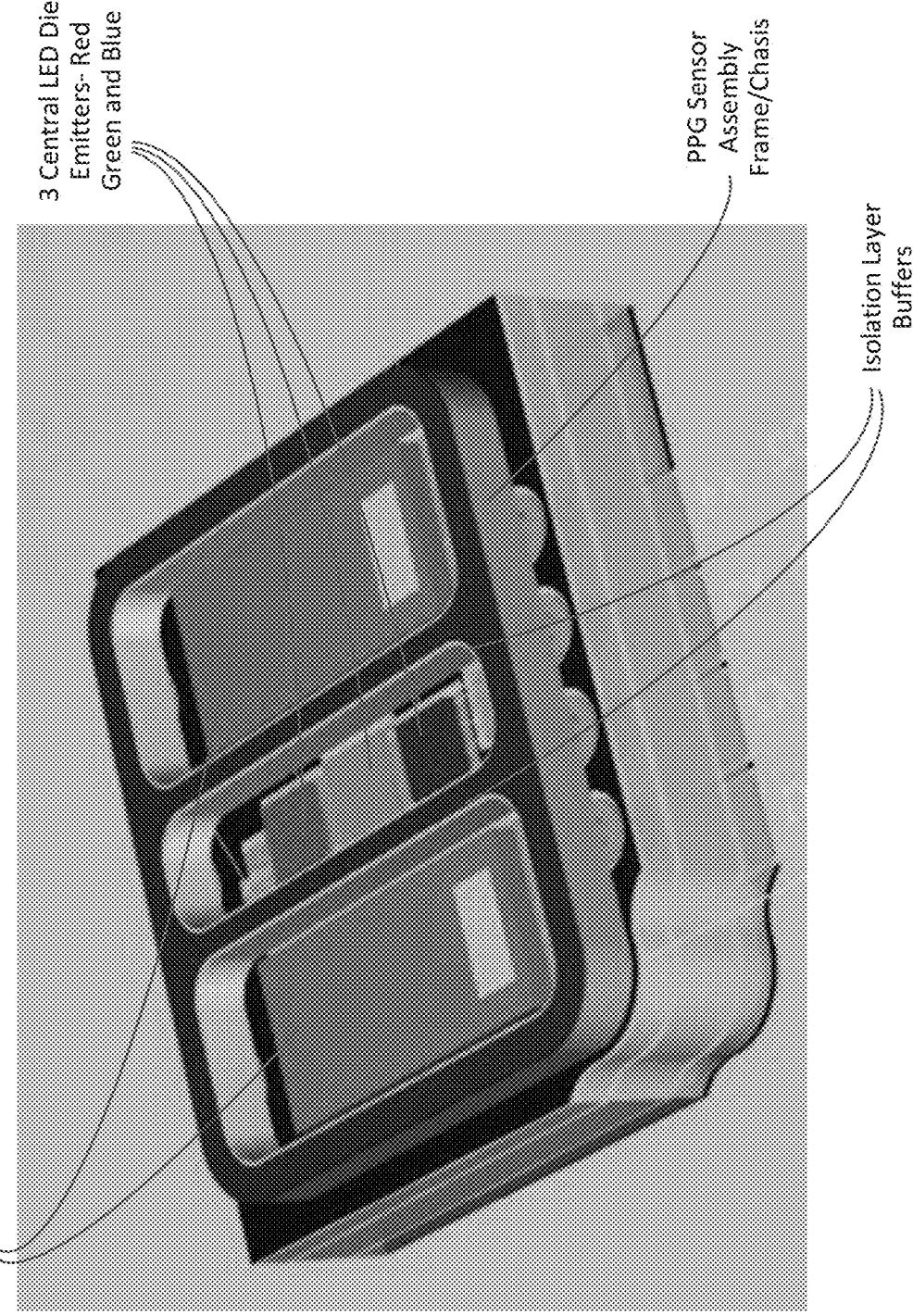
FIG. 3C, is a diagram of a third exemplary PPG sensor assembly, including red, green and blue light emitters, in accordance with some embodiments of the present invention.

Turning now to FIG. 3C, there is shown an isometric view diagram of a third exemplary PPG sensor configuration/assembly, in accordance with some embodiments of the present invention, wherein three LED dies/emitters—red, green and blue; or alternatively, infrared, red, and green—are positioned substantially in the center of the assembly. Two photodiode areas are shown below the LED emitters, wherein the two photodiodes areas are part of a single photodiode stretching over substantially the entire are of the framed section of the assembly. The shown photodiode areas are covered by tunable optical filters, in the form of a plate or a surface, and can be tuned to have different optical band passes. The tunable optical filter can be tuned to correspond (i.e. allow the passage of) one or more of the photon wavelengths of one or more of the red, green and/or blue emitters, or alternatively, the photon wavelengths of one or more of the infrared, red, and/or green emitters.

Figure 3D:
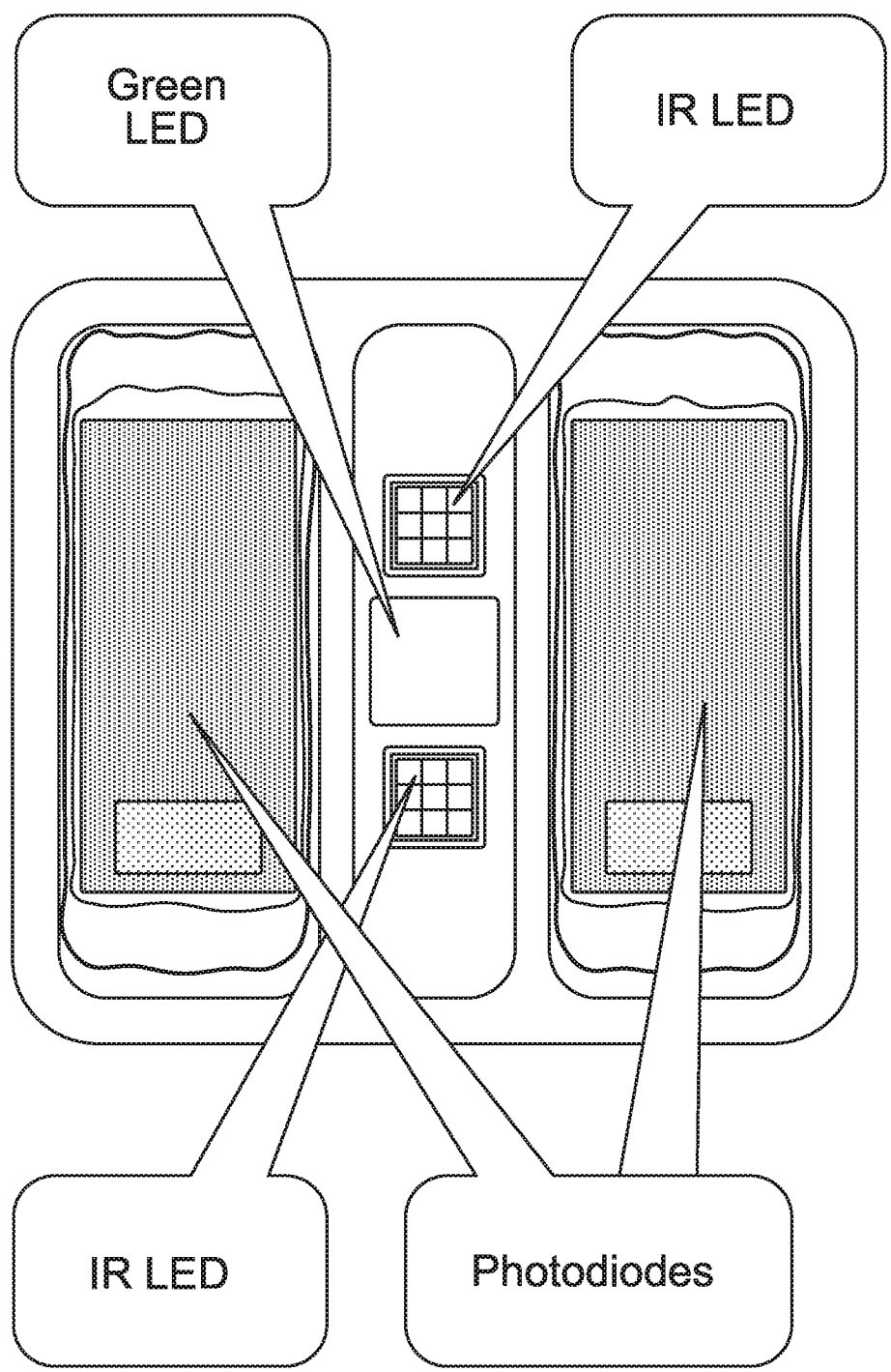
FIG. 3D, is a diagram of the third exemplary PPG sensor assembly, including infrared, red, and green light emitters, in accordance with some embodiments of the present invention.

Turning now to FIG. 3D, there is shown a bottom view (viewing from the subject skin side) diagram of a third exemplary PPG sensor configuration/assembly, in accordance with some embodiments of the present invention, wherein three LED dies/emitters—infrared, red, and green—are positioned substantially in the center of the assembly. Two photodiode areas are shown below the LED emitters, wherein the two photodiodes areas are part of a single photodiode stretching over substantially the entire are of the framed section of the assembly. The shown photodiode areas are covered by tunable optical filters, in the form of a plate or a surface, and can be tuned to have different optical band passes. The tunable optical filter can be tuned to correspond (i.e. allow the passage of) one or more of the photon wavelengths of one or more of the infrared, red and/or green emitters.

Figure 4A:
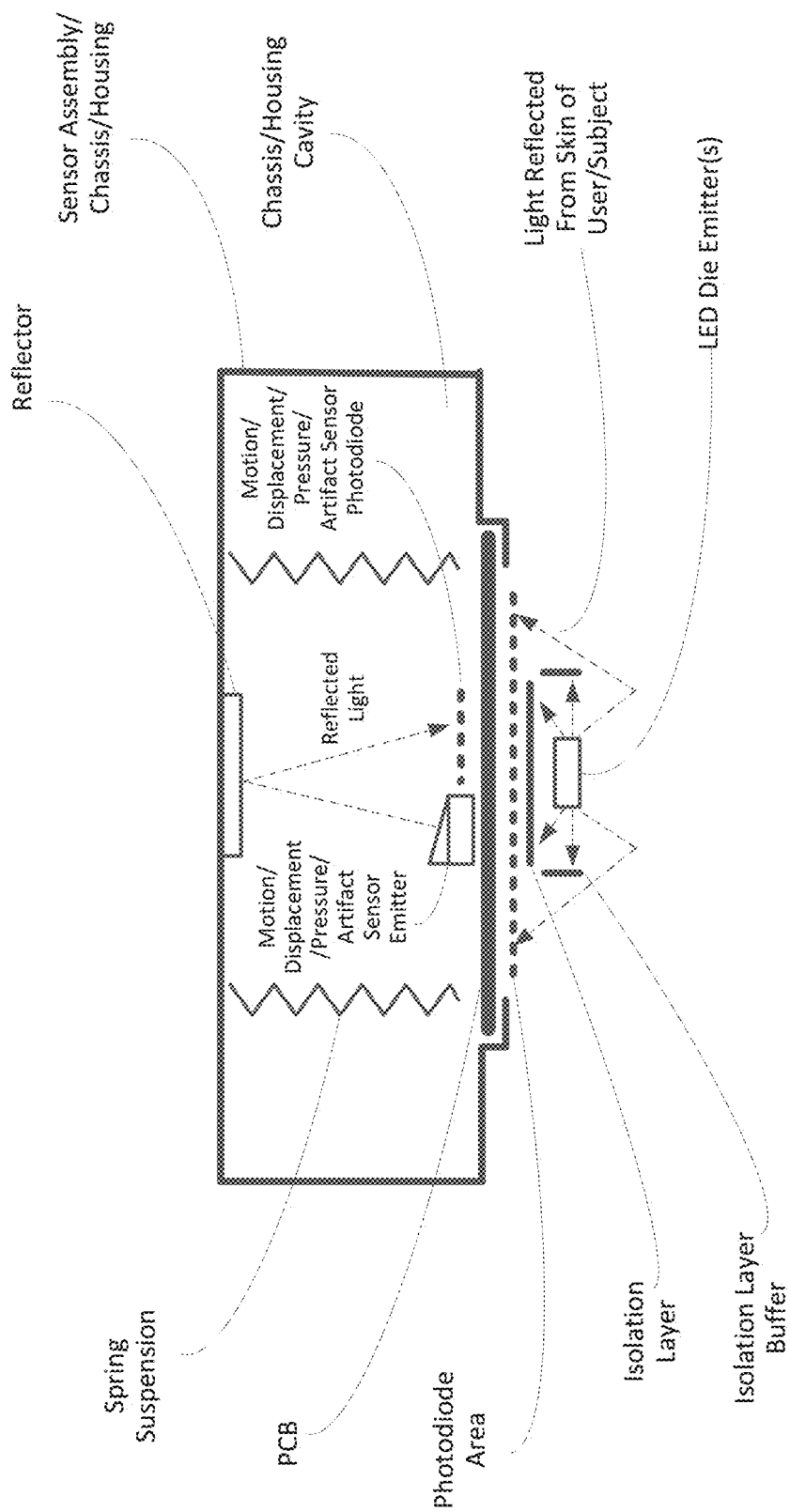
FIG. 4A, is a schematic diagram of an exemplary PPG sensor assembly with a PCB spring suspension, in accordance with some embodiments of the present invention.

Turning now to FIG. 4A, there is shown a cross sectional diagram of an exemplary sensor assembly, in accordance with some embodiments of the present invention, including a PPG sensor mounted on a contact surface of the assembly and an optical motion/displacement/pressure/artifact sensor facing an inner cavity of the assembly. Both sensors are positioned on opposite sides of the same printed circuit board (PCB), which printed circuit board is suspended on springs connecting the PCB to a chassis of the assembly.

The PPG sensor shown, includes two photodiode sensing apertures/areas, which are part of the same photodiode sensing surface, on either side of the shown emitter(s) unit. The emitter(s) are optically isolated from the photo-diode sensing aperture by optical isolation structure/layers made of non-transparent material. Surfaces, of each of the emitters of the emitter(s) unit, may be connected to the same or to different photo-emitters and may be angled (as exemplified in the figure) towards the photo-diode so as to focus emitted light onto and into the coverage area(s) of the photo-diodes.

The shown springs allows for the optical displacement sensor to move in sync with the PPG sensor. According to the embodiment shown, the displacement sensor includes an emitter whose emitted light is directed towards a reflector placed on an inner surface of the assembly cavity opposite from the emitter. The displacement sensor also includes a photodiode positioned in proximity with the emitter and configured to sense reflections of the emitter's light reflected by the reflector on the opposite side of the cavity. As the distance between the displacement sensor emitter, mounted on the inner surface of the suspended PCB, and the displacement sensor reflector changes due to movements of the PCB relative to the chassis forming the cavity to which the reflector is attached, the amplitude and/or phase of the light detected by the displacement sensor photodiode also changes. Accordingly, displacement/movement/pressure experienced by the PPG sensor may be measured.

Figure 4B:
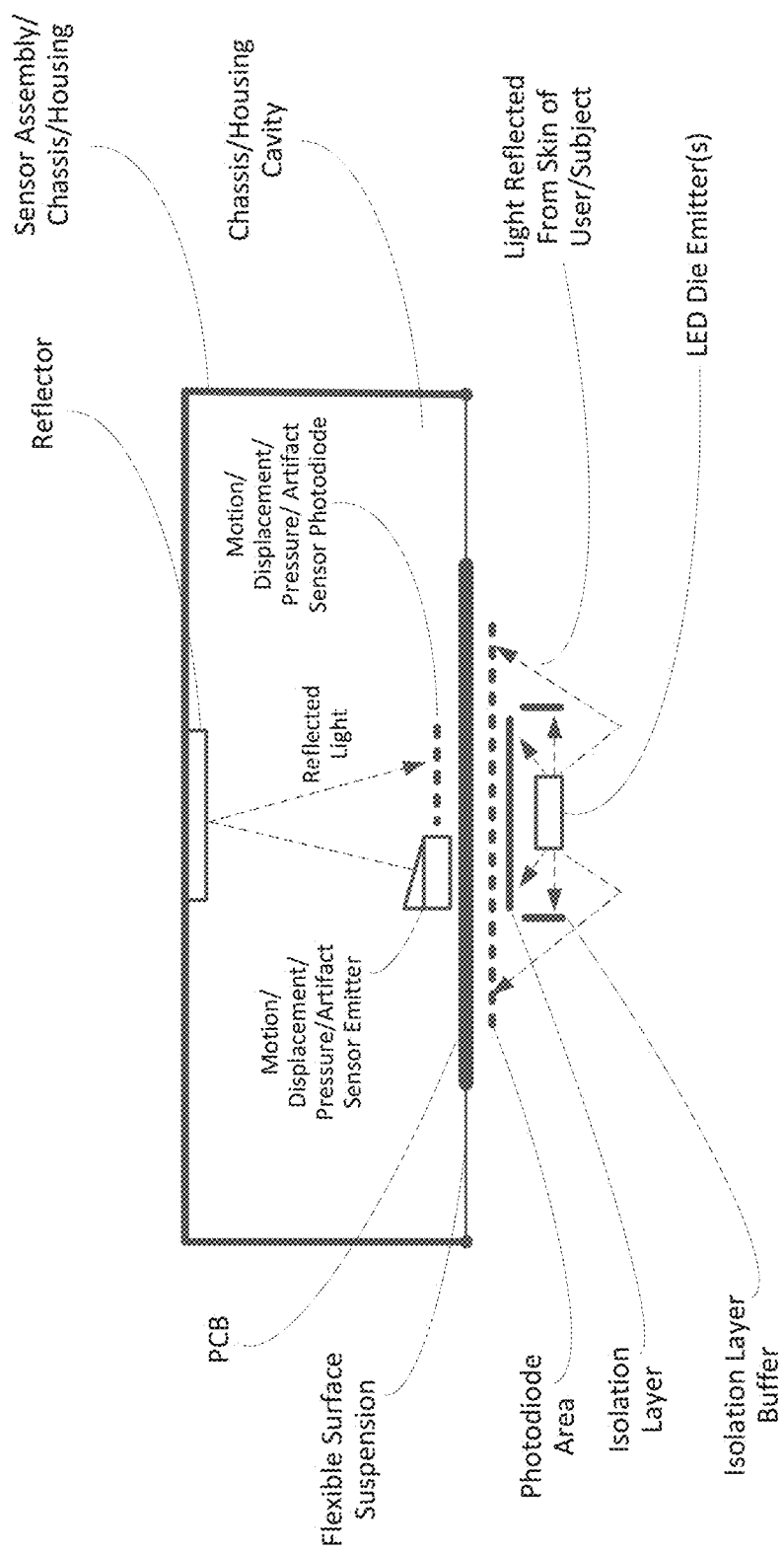
FIG. 4B, is a schematic diagram of an exemplary PPG sensor assembly with a PCB flexible surface suspension, in accordance with some embodiments of the present invention.

Turning now to FIG. 4B, there is shown a cross sectional diagram of an exemplary sensor assembly, in accordance with some embodiments of the present invention, including a PPG sensor mounted on a contact surface of the assembly and an optical motion/displacement/pressure/artifact sensor facing an inner cavity of the assembly. Both sensors are positioned on opposite sides of the same printed circuit board (PCB), which printed circuit board is suspended on a flexible surface connecting the PCB to a chassis of the assembly.

The PPG sensor shown, includes two photodiode sensing apertures/areas, which are part of the same photodiode sensing surface, on either side of the shown emitter(s) unit. The emitter(s) are optically isolated from the photo-diode sensing aperture by optical isolation structure/layers made of non-transparent material. Surfaces, of each of the emitters of the emitter(s) unit, may be connected to the same or to different photo-emitters and may be angled (as exemplified in the figure) towards the photo-diode so as to focus emitted light onto and into the coverage area(s) of the photo-diodes.

The shown flexible surface allows for the optical displacement sensor to move in sync with the PPG sensor. According to the embodiment shown, the displacement sensor includes an emitter whose emitted light is directed towards a reflector placed on an inner surface of the assembly cavity opposite from the emitter. The displacement sensor also includes a photodiode positioned in proximity with the emitter and configured to sense reflections of the emitter's light reflected by the reflector on the opposite side of the cavity. As the distance between the displacement sensor emitter, mounted on the inner surface of the suspended PCB, and the displacement sensor reflector changes due to movements of the PCB relative to the chassis forming the cavity to which the reflector is attached, the amplitude and/or phase of the light detected by the displacement sensor photodiode also changes. Accordingly, displacement/movement/pressure experienced by the PPG sensor may be measured.

Figure 5A:
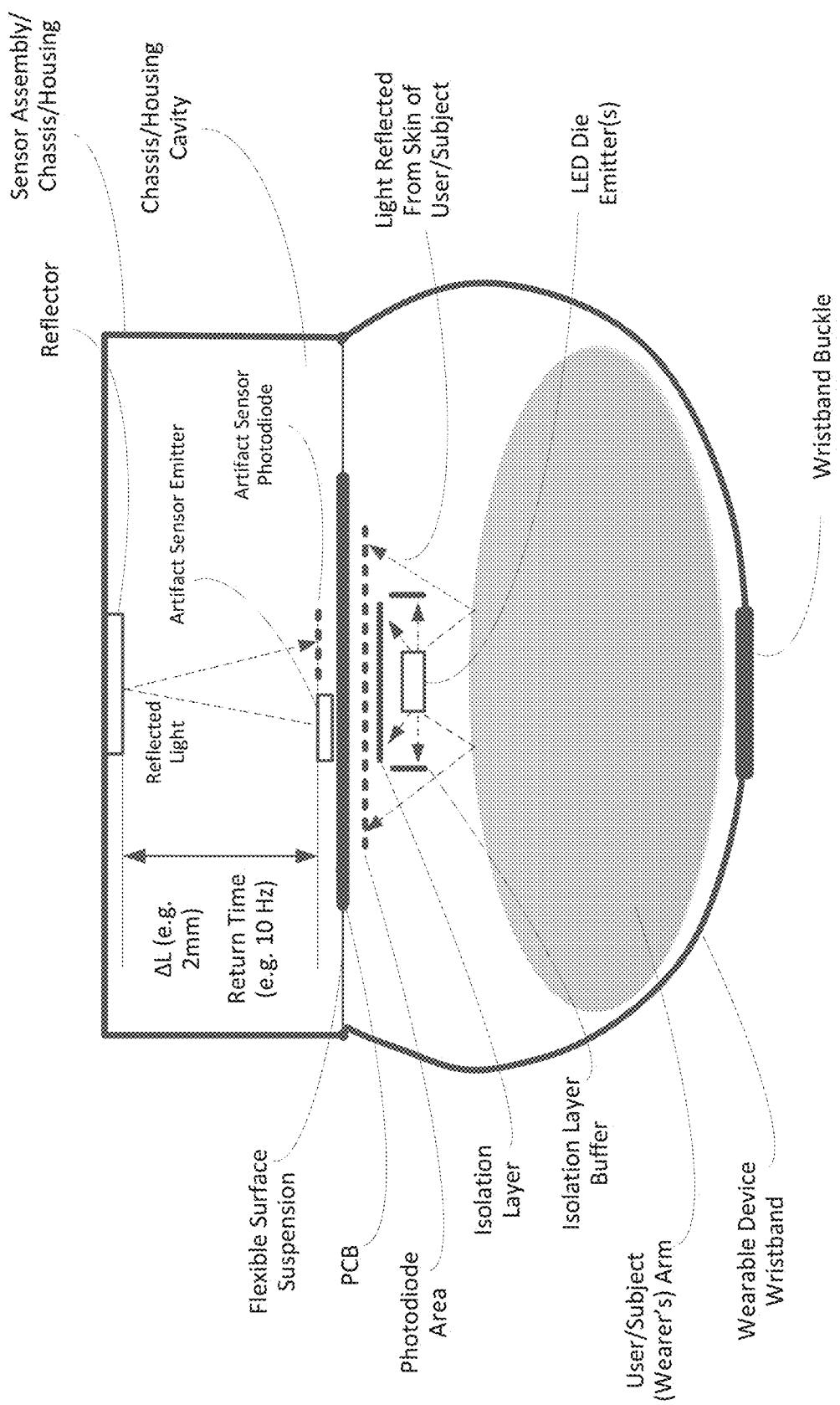
FIG. 5A, is a schematic diagram of an exemplary wearable device with a PPG PCB flexible surface suspension, in accordance with some embodiments of the present invention.

Turning now to FIG. 5A, there is shown a cross-section view of a wearable wristband device with a PPG PCB flexible surface suspension, in accordance with some embodiments of the present invention, wherein the wearable wristband shown is intended to hold the sensor assembly on/against the wrist of a user/subject.

The shown wristband includes an exemplary PPG sensor assembly, wherein an isolation layer and isolation layer buffers prevent light from the shown LED from traveling directly towards to the photodiode area. Accordingly, light hitting the photodiode area is substantially limited to light reflecting of the body (e.g. skin) of the user/subject (wearer) of the wristband. Further shown in the figure are the band and buckle of the wristband, the user's/subject's (wearer's) arm within the band, and the PCB on which the sensor configuration is implemented.

The shown cavity of the sensor assembly/chassis/housing may allow for the PCB connected by, and suspended on, the flexible surface suspension, along with the sensor configuration implemented thereon, to travel upwards and into the cavity as the user moves and creates tension or pressure on it. The suspended PCB shown, may optionally be rigid/inflexible and may optionally have a thickness of approximately 0.5 millimeters.

Figure 5B:
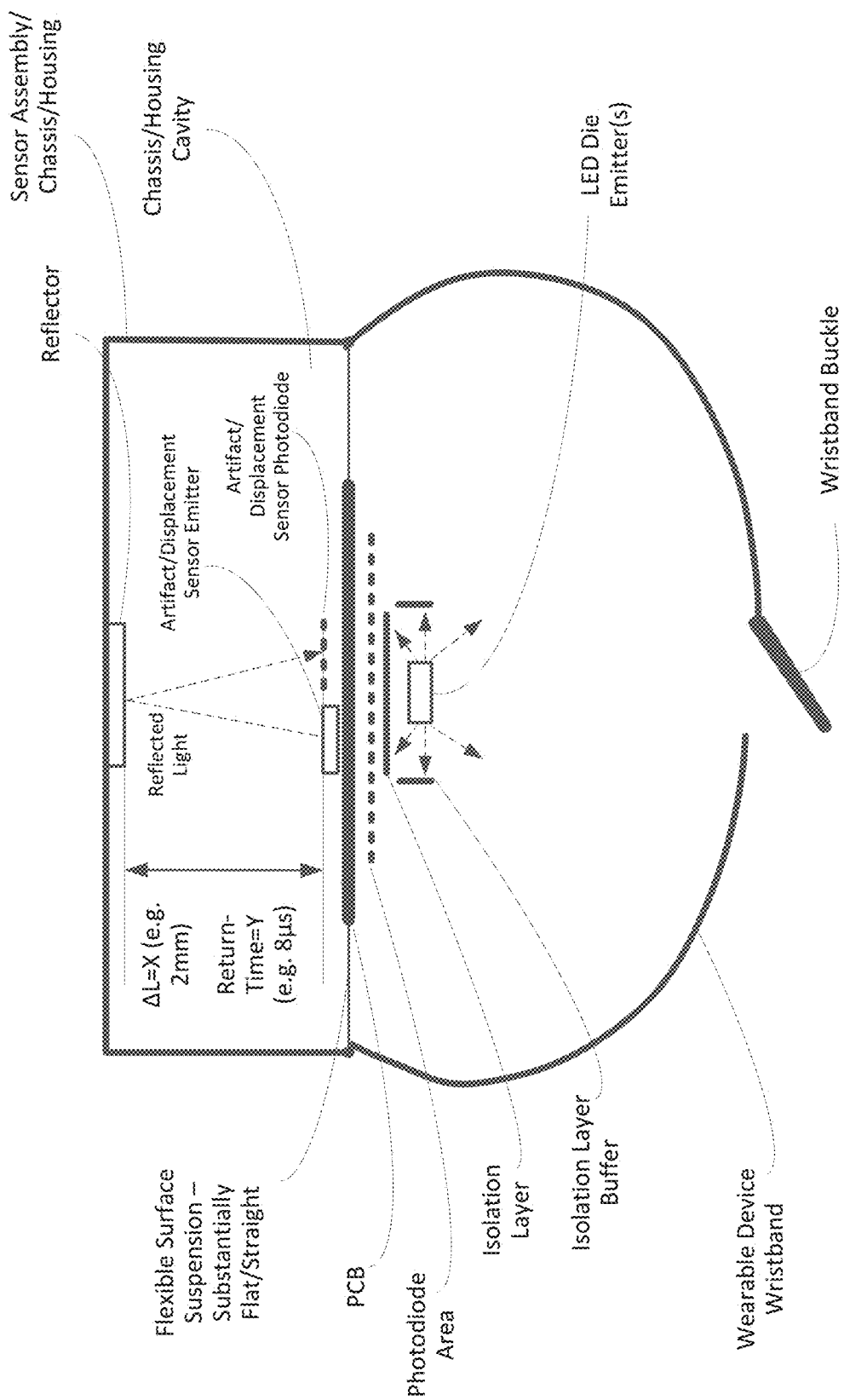
FIG. 5B, is a schematic diagram of an exemplary wearable device with a PPG PCB flexible surface suspension—prior to wearing, in accordance with some embodiments of the present invention.

Turning now to FIG. 5B, there is shown, in accordance with some embodiments of the present invention, a cross-section view of the wearable wristband device of FIG. 5A, wherein the wearable wristband device is shown prior to its wearing by the user/subject. As the wristband device is not being worn, the wristband buckle is shown to be open and the user's/subject's (wearer's) arm is not within/wrapped-by the band. The flexible surface suspension is shown to be substantially flat/straight as there is no tension or pressure applied onto the suspended PCB and/or sensor assembly/configuration implemented thereon (i.e. no user/subject motions).

Figure 5C:
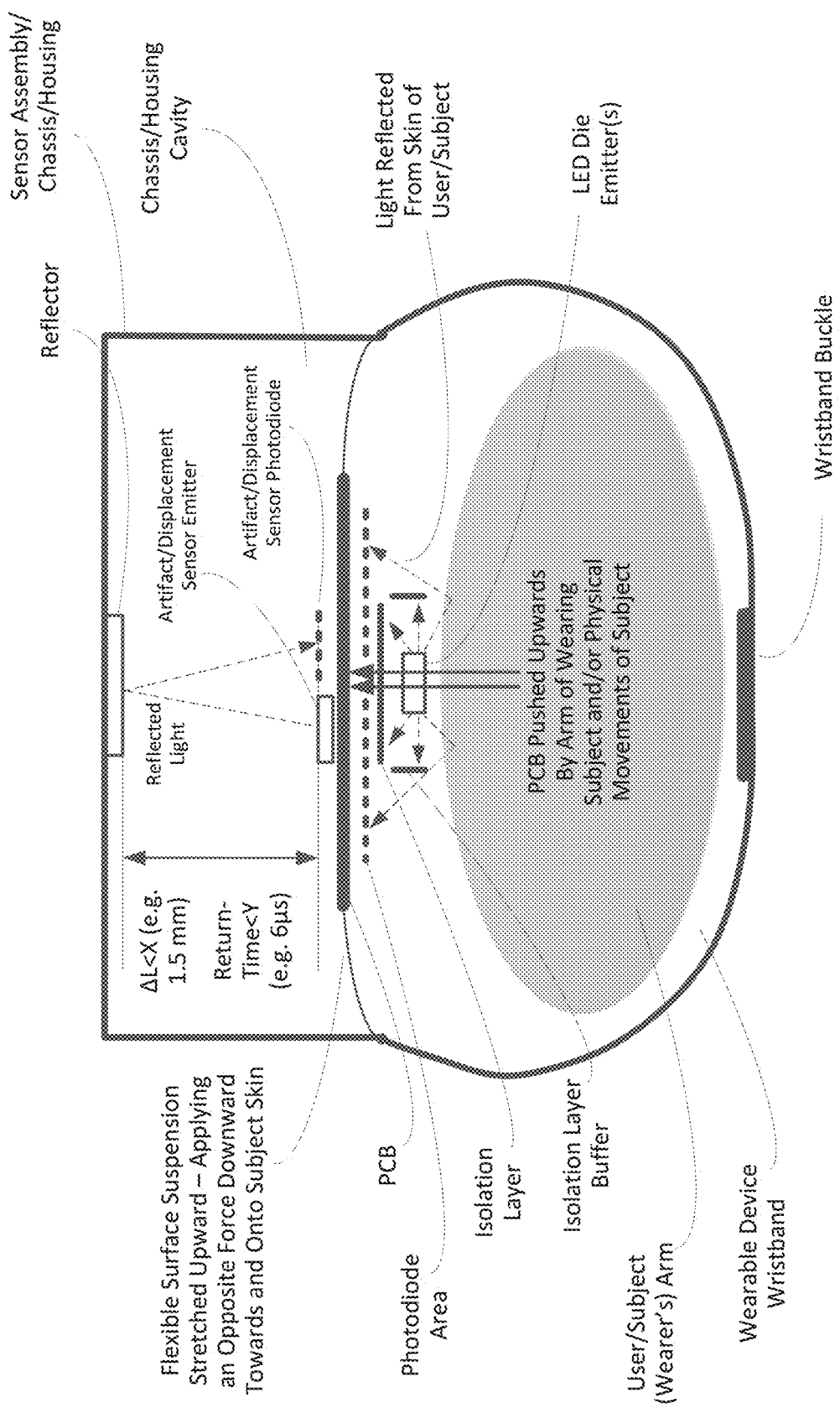
FIG. 5C, is a schematic diagram of an exemplary wearable device with a PPG PCB flexible surface suspension—after/during wearing, in accordance with some embodiments of the present invention.

Turning now to FIG. 5C, there is shown, in accordance with some embodiments of the present invention, a cross-section view of the wearable wristband device of FIG. 5A, wherein the wearable wristband device is shown during its wearing by the user/subject. As the wristband device is being worn, the wristband buckle is shown to be closed and the user's/subject's (wearer's) arm is within/wrapped-by the band. The flexible surface suspension is shown to be stretched upward—applying an opposite force downward and onto the skin of the wearing user/subject. The shown flexible surface suspension—stretched due to tension or pressure on the PCB and/or sensor assembly/configuration implemented thereon, being pushed upwards by the arm/wrist of the wearing user/subject and or his/her physical movements and/or physical motions—and is thus biased towards returning to its initial (FIG. 5B) bottom position, adjacent to the arm/wrist of the user/subject. As the tension or pressure is relieved the PCB may return to, or to the proximity of, its initial bottom position, and the flexible surface may become substantially flat/straight once again, or less stretched/bent.

Figure 5D:
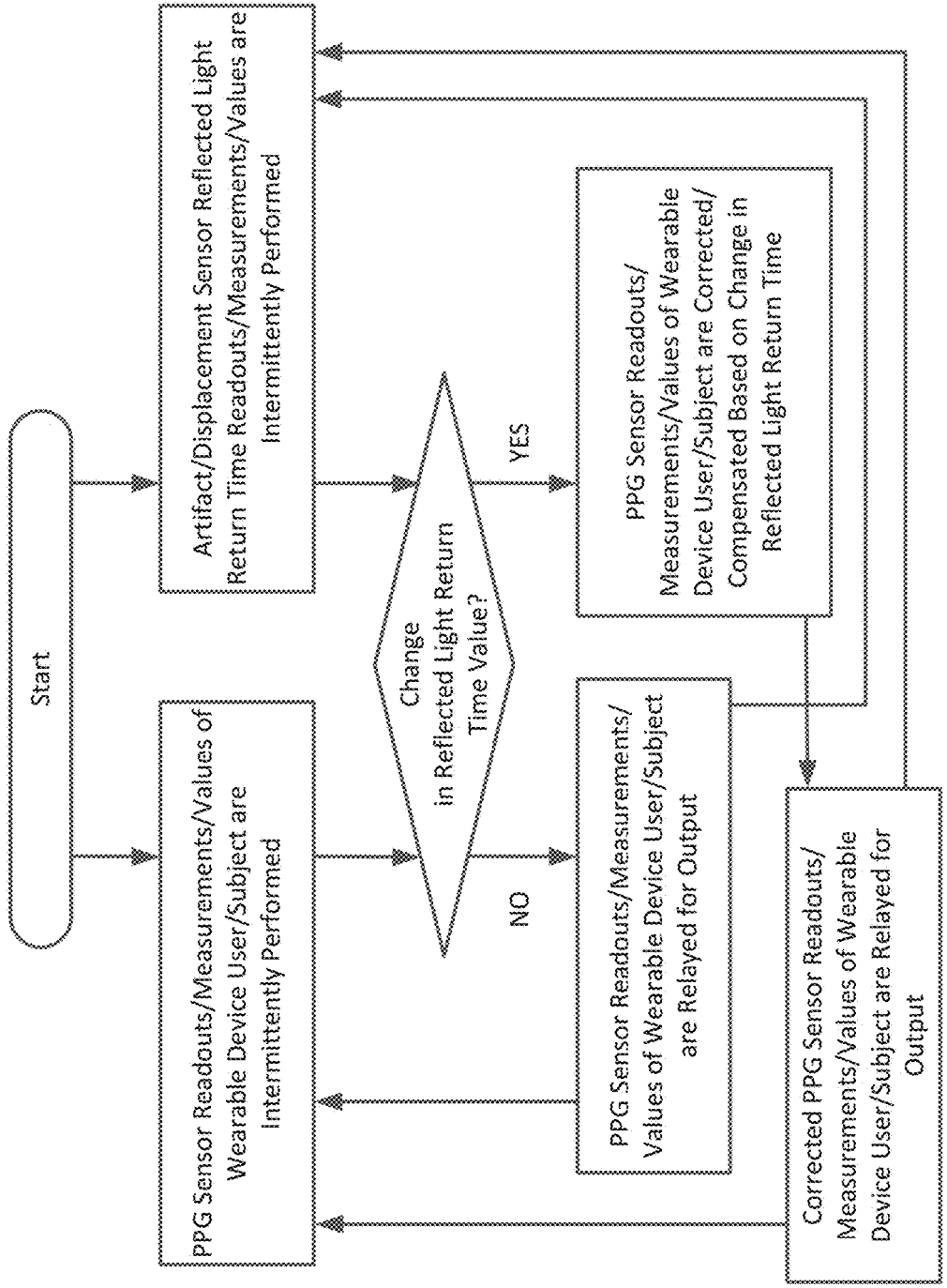
FIG. 5D, is a flowchart diagram of an exemplary artifact/displacement compensation process based on displacement sensor reflected light return time, in accordance with some embodiments of the present invention.

Turning now to FIG. 5D there is shown, in accordance with some embodiments of the present invention, a flowchart of an exemplary artifact/displacement compensation process based on displacement sensor reflected light return time. The shown process includes the following exemplary steps: (1) PPG sensor(s) readouts/measurements/values of wearable device user/subject are intermittently performed; (2) In parallel and/or alternatively, artifact/displacement sensor reflected light return time readouts/measurements/values are intermittently performed; (3) Reflected light return time measurement values are monitored;

(4) Performed PPG sensor readouts/measurements/values of wearable device user/subject are relayed for output (for example through: a visual output component, an audio output component and/or a communication transmitter of the wearable device); and (5) Upon detection of a change in the monitored reflected light return time value: (a) PPG Sensor readouts/measurements/values of wearable device user/subject are corrected/compensated based on change/deltas in reflected light return time and (b) corrected PPG sensor readouts/measurements/values of wearable device user/subject are relayed for output.

Figure 6:
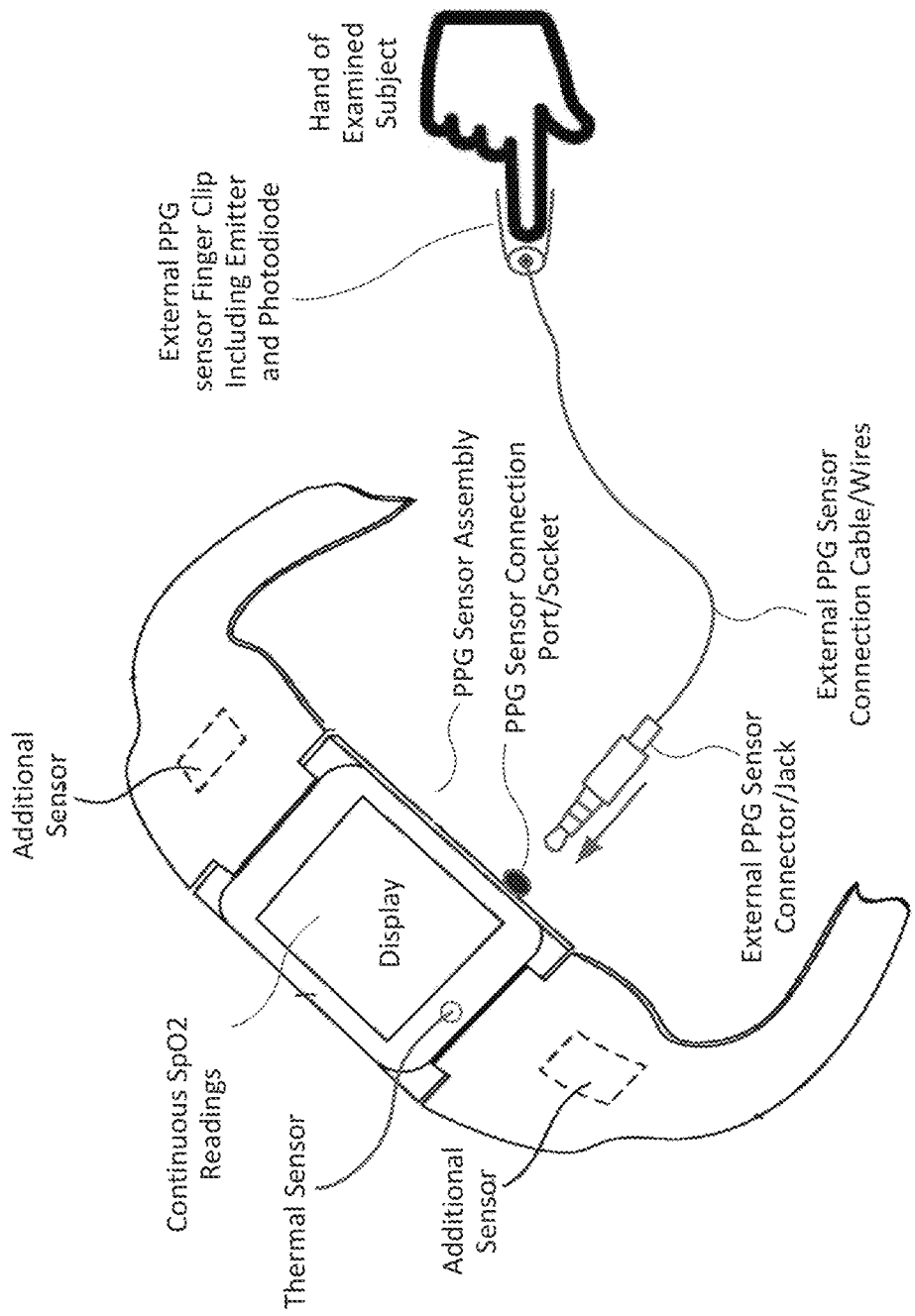
FIG. 6, is a schematic diagram of an exemplary external PPG sensor finger clip configuration for continuous SpO2 measurement, in accordance with some embodiments of the present invention.

Turning now to FIG. 6 there is shown, in accordance with some embodiments of the present invention, an illustration of the exemplary wearable device of FIG. 1, further including an exemplary external PPG sensor finger clip configuration for continuous SpO2 measurement. The shown external PPG sensor finger clip, includes at least an emitter(s) and a photodiode(s). Electric signals picked-up/sensed by the photodiode(s) are relayed to the wearable device over the external PPG sensor connection cable/wires, connected to the PPG sensor port/socket of the device by the external PPG connector/jack. The external PPG sensor finger clip may allow for continuous SpO2 monitoring, which readings are displayed over the display of the device and/or otherwise outputted or communicated for presentation, storage and/or further analysis/review.

Figure 7:
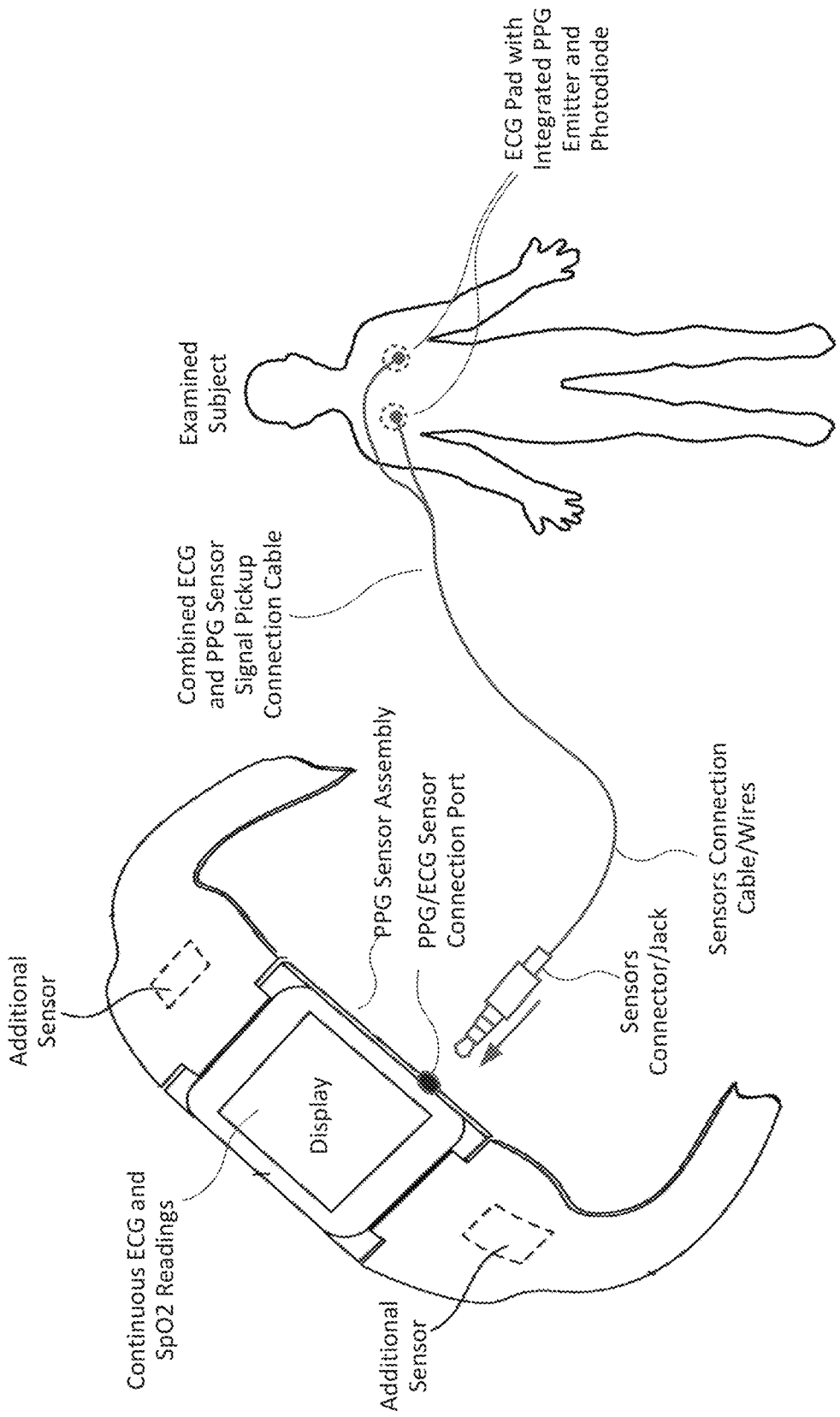
FIG. 7, is a schematic diagram of an exemplary combined ECG and PPG chest pad unit configuration, in accordance with some embodiments of the present invention.

Turning now to FIG. 7 there is shown, in accordance with some embodiments of the present invention, an illustration of the exemplary wearable device of FIG. 1, further including an exemplary external combined ECG pad(s) with an integrated PPG sensor for continuous ECG and SpO2 measurement. The shown external ECG pad(s) with integrated PPG, includes at least ECG electrode(s)/lead(s) a PPG emitter(s) and a PPG photodiode(s). Electric signals picked-up/sensed by the ECG and PPG components are relayed to the wearable device over the external combined pad sensor connection cable/wires, connected to the PPG/ECG sensor port/socket of the device by the external sensors connector/jack. The external combined ECG pad(s) with an integrated PPG sensor may allow for both, continuous SpO2 monitoring and continuous ECG monitoring, which readings are displayed over the display of the device and/or otherwise outputted or communicated for presentation, storage and/or further analysis/review.

According to some embodiments of the present invention, a composite bio-parameter sensor assembly for detecting vital signs of a subject person, may comprise: a printed circuit board (PCB); one or more first sensors, mounted on an outer contact surface of the assembly and having a sensing surface to optically detect one or more parameters of a pulse of the subject; and a second sensor, facing an inner cavity of the assembly, for optically detecting displacement of the one or more first sensors, wherein the one or more first sensors and the second sensor are positioned on the opposite sides of the PCB.

According to some embodiments, the composite bio-parameter sensor assembly may comprise a flexible surface suspendingly (i.e. in a suspended form/manner) connecting the PCB to a chassis of the assembly, such that both, the one or more first sensors and the second sensor positioned on the opposite sides of the PCB, are collectively correlated to the flexible surface, enabling them to move in sync with one another.

According to some embodiments, the second sensor of the composite bio-parameter sensor assembly may include at least a light emitter and a photodiode; and, may further comprise a reflector, positioned on an inner surface of the cavity of the assembly, substantially opposite of the emitter.

According to some embodiments, the composite bio-parameter sensor assembly may further comprise a processing logic for intermittently calculating, based on electric signal outputs of the photodiode of the second sensor, the distance, or change in distance, between the emitter of the second sensor and the reflector and for estimating the movement of the second sensor corresponding to the movement of the one or more first sensors moving in sync therewith based thereof; and for accordingly assessing the displacement experienced by the one or more first sensors and compensating for it.

According to some embodiments, of the composite bio-parameter sensor assembly, the one or more first sensors may be PPG sensors including one or more central light emitters and two or more photodiode areas that are part of a single photodiode surface, wherein the photodiode surface is positioned behind the emitter and at least partially sticks out from at least one of its sides.

According to some embodiments, of the composite bio-parameter sensor assembly, the one or more central light emitters may include: a red light emitter, a green light emitter and an infrared light emitter; and may further comprise an optical filter, in the form of a surface covering the photodiode areas of the PPG sensors, tunable to allow the passage of one or more of the photon wavelengths of one or more of the red, green and infrared light emitters.

According to some embodiments, of the composite bio-parameter sensor assembly, the flexible surface may be made from boPET.

According to some embodiments, the composite bio-parameter sensor assembly may further comprise a third sensor, of an ECG type, having an ECG sensing surface substantially aligned with the sensing surface of the first one or more PPG sensors, such that a subject touching the assembly concurrently comes in contact with both the ECG sensing surface of the ECG type sensor and the sensing surface of the first one or more PPG sensors.

According to some embodiments of the present invention, a wearable wristband device may include a composite bio-parameter sensor assembly connected thereto for detecting vital signs of a subject person, wherein the assembly comprises: a printed circuit board (PCB); one or more first sensors, mounted on an outer contact surface of the assembly and having a sensing surface to optically detect one or more parameters of a pulse of the subject; a second sensor, facing an inner cavity of the assembly, for optically detecting displacement of the one or more first sensors, wherein the one or more first sensors and the second sensor are positioned on the opposite sides of the PCB; and a flexible surface suspendingly (i.e. in a suspended form/manner) connecting the PCB to a chassis of the assembly, such that both, the one or more first sensors and the second sensor positioned on the opposite sides of the PCB, are collectively correlated to the flexible surface, enabling them to move in sync with one another, wherein upon the wearable wristband device being worn by a subject, the flexible surface is stretched and biased towards its original, substantially flat, pre worn shape, causing it and the contact surface of the one or more first sensors suspended thereon, to retain contact, of approximately the same force, with the skin of the subject wearing the device.

According to some embodiments, the wearable wristband device may further comprise an external connection port for receiving a connector of an external sensor component.

According to some embodiments, of the wearable wristband device, the external sensor component may be a sensor pad, including sensor elements selected from the group consisting of: a PPG sensor light emitter and photodiode, ECG sensor electrodes and/or a combination of both a PPG sensor light emitter and photodiode and ECG sensor electrodes.

According to some embodiments, of the wearable wristband device, the external sensor component elements may facilitate the continuous measurement of SpO2 or ECG bio parameters of the subject.

According to some embodiments, of the wearable wristband device the external sensor component elements may facilitate the continuous measurement of both SpO2 and ECG bio parameters of the subject.

According to some embodiments, the wearable wristband device may further comprise an optical thermal sensor, located at an outer position of the wearable device and functionally connected with circuitries of at least a processing logic and a control logic of the first sensors and the second sensor incorporated into the assembly of the wearable device.

According to some embodiments, the wearable wristband device may further comprise outer ECG sensor electrodes located at an outer position of the wearable device and functionally connected with circuitries of at least a processing logic and a control logic of the first sensors and the second sensor incorporated into the composite bio-parameter.

According to some embodiments, of the wearable wristband device, the outer ECG sensor electrodes are positioned over a user interface element, allowing for the control logic to sense the contact of an engaging subject and in response, to trigger ECG measurements of the subject.

According to some embodiments, of the wearable wristband device, the second sensor, of the composite bio-parameter sensor assembly, may include at least a light emitter and a photodiode; and, may further comprise a reflector, positioned on an inner surface of the cavity of the assembly, substantially opposite of the emitter.

According to some embodiments, of the wearable wristband device, the one or more first sensors, of the composite bio-parameter sensor assembly, may be PPG sensors including one or more central light emitters and two or more photodiode areas that are part of a signal photodiode surface, wherein the photodiode surface is positioned behind the emitter and at least partially sticks out from at least one of its sides.

According to some embodiments, of the wearable wristband device, the one or more central light emitters may include: a red light emitter, a green light emitter and an infrared light emitter; wherein, the composite bio-parameter sensor assembly further comprises an optical filter, in the form of a surface covering the photodiode areas of the PPG sensors, tunable to allow the passage of one or more of the photon wavelengths of one or more of the red, green and infrared light emitters.

According to some embodiments, of the composite bio-parameter sensor assembly, the one or more first sensors may be PPG sensors including one or more central light emitters and two or more separate photodiode surfaces wherein the photodiode surfaces are positioned behind the emitters and at least partially stick out from at least one of the sides of each of the emitters; wherein the one or more central light emitters include: an infrared light emitter, a red light emitter, a green light emitter and a blue light emitter; and further comprise an optical filter, in the form of one or more surfaces covering at least some of the photodiode surfaces of the PPG sensors, tunable to allow the passage of one or more of the photon wavelengths of one or more of the infrared, red, green and blue light emitters.

According to some embodiments, the wearable wristband device may further comprise a thermal sensor, wherein the thermal sensor is positioned in an outer location of the device, enabling the direction of the thermal sensor into an open mouth of a device wearing subject, in order to measure the subject's core body temperature.

The subject matter described above is provided by way of illustration only and should not be constructed as limiting. While certain features of the invention have been illustrated and described herein, many modifications, substitutions, changes, and equivalents will now occur to those skilled in the art. It is, therefore, to be understood that the appended claims are intended to cover all such modifications and changes as fall within the true spirit of the invention.

The invention claimed is:

1. A composite bio-parameter sensor assembly for detecting vital signs of a subject person, said assembly comprising:
   a housing that comprises an inner cavity and a contact surface having a sensing surface on an exterior of the housing;
   a printed circuit board (PCB) disposed at least partially within the housing;
   one or more first sensors, facing said contact surface to optically detect one or more parameters of a pulse of the subject; and
   a second sensor, facing said inner cavity, for optically detecting displacement of said one or more first sensors with respect to the housing, wherein said one or more first sensors and said second sensor are positioned on the opposite sides of said PCB.

2. The composite bio-parameter sensor assembly of claim 1, further comprising:
   a flexible surface suspendingly connecting said PCB to a chassis of said assembly, such that both, said one or more first sensors and said second sensor positioned on the opposite sides of said PCB, are collectively correlated to the flexible surface, enabling them to move in sync with one another.

3. The composite bio-parameter sensor assembly of claim 2, wherein said second sensor includes at least a light emitter and a photodiode; and, further comprising a reflector, positioned on the inner cavity of said housing, substantially opposite of the emitter.

4. The composite bio-parameter sensor assembly of claim 3, further comprising a processing logic for intermittently calculating, based on electric signal outputs of the photodiode of said second sensor, the distance, or change in distance, between the emitter of said second sensor and said reflector and for estimating the movement of said second sensor corresponding to the movement of said one or more first sensors moving in sync therewith based thereof; and for accordingly assessing the displacement experienced by said one or more first sensors and compensating for it.

5. The composite bio-parameter sensor assembly of claim 2, wherein said one or more first sensors are PPG sensors including one or more central light emitters and two or more photodiode areas that are part of a single photodiode.

6. The composite bio-parameter sensor assembly of claim 5, wherein said one or more central light emitters include: a red light emitter, a green light emitter and an infrared light emitter; and farther comprising an optical filter, in the form of a surface covering said photodiode areas of said PPG sensors, tunable to allow the passage of one or more of the photon wavelengths of one or more of said red, green and infrared light emitters.

7. The composite bio-parameter sensor assembly of claim 5, further comprising an ECG sensor having an ECG sensing surface substantially aligned with the sensing surface of said first one or more PPG sensors, such that a subject touching said assembly concurrently comes in contact with both the ECG sensing surface of said ECG sensor and the sensing surface of said first one or more PPG sensors.

8. The composite bio-parameter sensor assembly of claim 2, wherein said flexible surface is made from biaxially oriented polyethylene terephthalate (boPET).

9. The composite bio-parameter sensor assembly of claim 2, wherein said one or more first sensors are PPG sensors including one or more central light emitters and two or more separate photodiode surfaces; wherein said one or more central light emitters include: an infrared light emitter, a red light emitter, a green light emitter and a blue light emitter;

and further comprising an optical filter, in the form of one or more surfaces covering at least some of said photodiode surfaces of said PPG sensors, tunable to allow the passage of one or more of the photon wavelengths of one or more of said infrared, red, green and blue light emitters.

10. A wearable wristband device including a composite bio-parameter sensor assembly connected thereto for detecting vital signs of a subject person, said composite bio-parameter assembly comprising:
- a housing that comprises an inner cavity and a contact surface having a sensing surface on an exterior of the housing;
- a printed circuit board (PCB) disposed at least partially within the housing;
- one or more first sensors, facing said contact surface to optically detect one or more parameters of a pulse of the subject;
- a second sensor, facing an inner cavity of the assembly, for optically detecting displacement of said one or more first sensors with respect to the housing, wherein said one or more first sensors and said second sensor are positioned on the opposite sides of said PCB; and
- a flexible surface suspendingly connecting said PCB to a chassis of said assembly, such that both, said one or more first sensors and said second sensor positioned on the opposite sides of said PCB, are collectively correlated to the flexible surface, enabling them to move in sync with one another, wherein upon said wearable wristband device being worn by a subject, said flexible surface is stretched and biased towards its original, substantially flat, pre worn shape, causing it and said contact surface to retain contact with the skin of the subject wearing said device.

11. The wearable wristband device of claim 10, further comprising an external connection port for receiving a connector of an external sensor component.

12. The wearable wristband device of claim 11, wherein said external sensor component is a sensor pad, including sensor elements selected from the group consisting of: (1) a PPG sensor light emitter and photodiode, (2) ECG sensor electrodes and (3) a combination of both a PPG sensor light emitter and photodiode and ECG sensor electrodes.

13. The wearable wristband device of claim 12, wherein said external sensor component elements facilitate the continuous measurement of SpO2 or ECG bio parameters of the subject.

14. The wearable wristband device of claim 12, wherein said external sensor component elements facilitate the continuous measurement of both SpO2 and ECG bio parameters of the subject.

15. The wearable wristband device of claim 12, further comprising an optical thermal sensor, disposed at an exterior of said housing and functionally connected with circuitries of at least a processing logic and a control logic of said first sensors and said second sensor incorporated into said assembly of the wearable device.

16. The wearable wristband device of claim 12, further comprising ECG sensor electrodes disposed at an exterior of said housing and functionally connected with circuitries of at least a processing logic and a control logic of said first sensors and said second sensor incorporated into said composite bio-parameter assembly.

17. The wearable wristband device of claim 16, wherein said ECG sensor electrodes are positioned over a user interface element, allowing for said control logic to sense the contact of an engaging subject and in response, to trigger ECG measurements of the subject.

18. The wearable wristband device of claim 10, wherein said second sensor, of said composite bio-parameter sensor assembly, includes at least a light emitter and a photodiode; and, further comprises a reflector, positioned on the inner cavity of said housing, substantially opposite of the emitter.

19. The wearable wristband device of claim 10, wherein said one or more first sensors, of said composite bio-parameter sensor assembly, are PPG sensors including one or more central light emitters and two or more photodiode areas that are part of a signal photodiode surface.

20. The wearable wristband device of claim 19, wherein said one or more central light emitters include: a red light emitter, a green light emitter and an infrared light emitter; and wherein, said composite bio-parameter sensor assembly further comprises an optical filter, in the form of a surface covering said photodiode areas of said PPG sensors, tunable to allow the passage of one or more of the photon wavelengths of one or more of said red, green and infrared light emitters.

21. The wearable wristband device of claim 10, further comprising a thermal sensor, wherein said thermal sensor is disposed on an exterior of the housing, enabling the direction of said thermal sensor into an open mouth of a device wearing subject, in order to measure the subject's core body temperature.

* * * * *